US009550746B2

(12) United States Patent
Yuan et al.

(10) Patent No.: US 9,550,746 B2
(45) Date of Patent: *Jan. 24, 2017

(54) BENZOFURAN-2-SULFONAMIDES DERIVATIVES AS CHEMOKINE RECEPTOR MODULATORS

(71) Applicant: Allergan, Inc., Irvine, CA (US)

(72) Inventors: Haiqing Yuan, Irvine, CA (US); Richard L. Beard, Newport Beach, CA (US); Xiaoxia Liu, Lake Forest, CA (US); John E. Donello, Dana Point, CA (US); Veena Viswanath, Irvine, CA (US); Michael E. Garst, Newport Beach, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/589,681

(22) Filed: Jan. 5, 2015

(65) Prior Publication Data

US 2015/0218119 A1 Aug. 6, 2015

Related U.S. Application Data

(63) Continuation of application No. 13/782,159, filed on Mar. 1, 2013, now Pat. No. 8,927,544.

(60) Provisional application No. 61/605,300, filed on Mar. 1, 2012.

(51) Int. Cl.
| C07D 307/78 | (2006.01) |
| C07D 405/12 | (2006.01) |
| C07D 307/82 | (2006.01) |
| C07D 405/14 | (2006.01) |

(52) U.S. Cl.
CPC ........... *C07D 307/78* (2013.01); *C07D 307/82* (2013.01); *C07D 405/12* (2013.01); *C07D 405/14* (2013.01)

(58) Field of Classification Search
CPC ... C07D 307/78; C07D 307/82; C07D 405/12; C07D 405/14
See application file for complete search history.

(56) References Cited

U.S. PATENT DOCUMENTS

| 7,393,873 B2 | 7/2008 | Anthony |
| 7,622,583 B2 | 11/2009 | Ungashe |
| 7,884,110 B2 | 2/2011 | Krasinski |
| 7,931,909 B2 | 4/2011 | Hughes |
| 8,927,544 B2 | 1/2015 | Yuan et al. |
| 2007/0037794 A1 | 2/2007 | Ungashe |
| 2008/0293720 A1 | 11/2008 | Cleary |
| 2011/0118248 A1 | 5/2011 | Ungashe |
| 2012/0014997 A1 | 1/2012 | Ungashe |

FOREIGN PATENT DOCUMENTS

| WO | 03-099773 | 4/2003 |
| WO | 2005016896 | 2/2005 |
| WO | 2008-008374 | 1/2008 |
| WO | 2008-010934 | 1/2008 |
| WO | 2012-082633 | 6/2012 |

OTHER PUBLICATIONS

Ambati, Jayakrishna et al, An Animal Model of Age-Related Macular Degeneration in Senescent Ccl-2- or Ccr-2Deficient Mice, Nature Medicine, 2003, 1390-1397, 9.
Beech, John et al, Neuroprotection in Ischemia-Reperfusion Injury: An Antiinflammatory Approach Using a Novel Broad-Spectrum Chemokine Inhibitor, Journal of Cerebral Blood Flow and Metabolism, 2001, 683-689, 21.
Database Registry Chemical Abstracts Service, Database Accession No. 1394718-08-1, Sep. 18, 2012.
Fang, I-Mo et al, Expression of chemokine and receptors in Lewis rats with experimental autoimmune anterior uveitis, Experimental Eye Research, 2004, 1043-1055, 78, US.
Feria, Manuel et al, The CCR2 Receptor as a Therapeutic Target, Expert Opin. Ther Patents, 2006, 49-57, 16.
Gerard, Craig et al, Chemokines and Disease, nature immunology, Chemokine Reviews, 2001, 108-115, 2, Nature Publishing Group.
Keino, Kiroshi et al, Chemokine and Chemokine Receptor Expression During Experimental Autoimmune Uveoretinitis in Mice, Graefe's Arch Clin Exp Ophthalmol, 2003, 111-115, 241.
Klitgaard, Torben et al, Chemokine Receptors and Early Activation Markers in Acute Anterior Uveitis, Acta Ophthalmol, Scand., 2004, 179-183, 82.
Meleth, Annal et al, Serum Inflammatory Makers in Diabetic Retinopathy, Investigative Ophthalmology & Visual Science, Nov. 2005, 4295-4301, 46.
Reckless, Jill et al, Identification of Oligopeptide Sequences Which Inhibit Migration Induced by a Wide Range of Chemokines, Biochem. J., 1999, 803-811, 340, GB.
Stahl, Heinrich et al, Handbook of Pharmaceutical Salts, Verlag Helvetica Chimica Acta—Zurich, 2002, 329-345.
Takeuchi, Aya et al, CCR5-Deficient Mice Develop Experimental Autoimmune Uveoretinitis in the Context of a Deviant Effector Response, Investigative Ophthalmology & Visual Science, Oct. 2005, 3753-3760, 46, US.
Tokuyama, Hirotake et al, The Simultaneous Blockage of Chemokine Receptors CCR2, CCR5 and CXCR3 by a Non-peptide Chemokine Receptor Antagonist Protects Mice From Dextran Sodium Sulfate-Mediated Colitis, International Immunology, 2005, 1023-1034, 17, US.
Tuaillon, Nadine et al, MCP-1 Expression in Endotoxin-Induced Uveitis, Investigative Ophthalmology & Visual Science, May 2002, 1493-1498, 43.
Wallace, Graham et al, The Role of Chemokines and Their Receptors in Ocular Disease, Progress in Retinal and Eye Research, 2004, 435-448, 23, Elsevier Ltd.
Weisberg, Stuart et al, CCR2 Modulates Inflammatory and Metabolic Effects of High-Fat Feeding, The Journal of Clinical Investigation, Jan. 2006, 115-124, 116.

(Continued)

*Primary Examiner* — Savitha Rao
*Assistant Examiner* — Angela Brown-Pettigrew
(74) *Attorney, Agent, or Firm* — Jonathan Bass

(57) ABSTRACT

The present invention relates to novel benzofuran-2-sulfonamide derivatives, processes for preparing them, pharmaceutical compositions containing them and their use as pharmaceuticals as modulators of chemokine receptors.

4 Claims, No Drawings

(56) References Cited

OTHER PUBLICATIONS

Wells, Timothy et al, Chemokine blockers—therapeutics in the making?, TRENDS in Pharmacological Sciences, Jan. 2006, 41-47, 27.

Yamagami, Satoru et al, CCR5 Chemokine Receptor Mediates Recruitment of MHC Class II—Positive Langerhans Cells in the Mouse Corneal Epithelium, Investigative Ophthalmology & Visual Science, Apr. 2005, 1201-1207, 46.

Yang, Chang-Hao et al, Effects of the NF-κB Inhibitor Pyrrolidine Dithiocarbamate on Experimentally Induced Autoimmune Anterior Uveitis, Investigative Ophthalmology & Visual Science, 2005, 1339-1347, 46.

Katritzky et al., Journal F. Prakt. Chemie. Band 332, Heft 6, 1990, S. 870-884.

Patent Cooperation Treaty, Nofitication of Transmittal of the International Search Report and the Written Opinion of the International Searching Authority, or the Declaration, PCT Application No. PCT/US2013/028599, mailed May 14, 2013.

BENZOFURAN-2-SULFONAMIDES DERIVATIVES AS CHEMOKINE RECEPTOR MODULATORS

RELATED APPLICATION

This application is a continuation of U.S. patent application Ser. No. 13/782,159 filed on Mar. 1, 2013 which in turn claims the benefit of U.S. Provisional Application Ser. No. 61/605,300, filed Mar. 1, 2012, each which is incorporated herein by reference in their entirety and serve as the basis for a priority and/or benefit claim.

FIELD OF THE INVENTION

The present invention relates to novel benzofuran-2-sulfonamide derivatives, processes for preparing them, pharmaceutical compositions containing them and their use as pharmaceuticals as modulators of chemokine receptors. The invention relates specifically to the use of these compounds and their pharmaceutical compositions to treat disorders associated with chemokine receptor modulation.

BACKGROUND OF THE INVENTION

Chemokines are a group of 7- to 14-kd peptides that play an important role in orchestrating leukocyte recruitment and migration during inflammation, and therefore represent an important target for anti-inflammatory therapies (Wells et al., 2006). They act by binding to seven-transmembrane, G protein-coupled receptors, the chemokine receptors. The chemokine system is complex, with about 50 chemokines and 20 chemokine receptors identified in humans, often acting with redundancy, making selection of specific antagonists difficult (Gerard and Rollins, 2001). Genetic knockout strategies have confirmed the importance of chemokines as regulators of immune function, but the deletion of specific chemokines has led to only specific and relatively mild defects in the inflammatory response further emphasizing the complex redundancy of the system. Selectivity is crucial for use of chemokine receptor antagonists in systemic diseases where a single chemokine-receptor system is implicated such as atheroscelorsis where the macrophage/monocyte system is the major player in order to allow a subtle and specific control over immune function (Weisberg et al., 2006; Feria and Diaz Gonzalez et al., 2006).

Many ocular conditions are characterized by inappropriate migration and infiltration of cells such as leukocytes and endothelial cells into the eye with deleterious effects to ocular structures (Wallace et al., 2004). Chemokines have been identified in such diseases and misregulation of the chemokine system is apparent in corneal graft rejection, diabetic retinopathy, age-related macular degeneration (ARMD), chronic inflammatory diseases such as uveitis, dry eye etc. Mice lacking CCR2 or MCP-1 develop features of ARMD with age, including drusen deposits, choroidal neovascularization and photoreceptor atrophy indicating a crucial role for this chemokine and its receptor signaling (Amabati et al., 2003). Thus CCR2 receptor-specific inhibitor might have potential therapeutic benefit in ocular diseases like ARMD. In contrast, various human and animal studies have identified several chemokines in different forms of uveitis, produced both by resident and infiltrating cells, that strongly suggests a prominent role for these molecules in its pathogenesis. Studies in rat and mice models of uveitis have demonstrated up-regulation of monocyte chemoattractant protein-1 (MCP-1), macrophage inflammatory protein-1 (MIP-1), RANTES, stromal derived factor-1 (SDF-1) which are powerful chemoattractants for monocytes and T-cells (Fang et al., 2004; Keino et al., 2003). Similar findings have been reported in peripheral blood mononuclear cells in patients with acute anterior uveitis (AAU), the most common form of human uveitis (Klitgaard et al., 2004). MCP-1 knockout mice and CCR5 knockout mice show reduced endotoxin-induced uveitis, which is the animal model for AAU (Takeuchi et al., 2005; Tuallion et al., 2002). It has also been demonstrated that blocking the chemokine system upstream with the use of NF-κB blockers significantly attenuates experimental AAU in rats (Yang et al., 2005). Blockage of NF-κB results in transcriptional inhibition of multiple chemokines. Given the complexity of pathogenesis in uveitis it is unlikely that a selective inhibition of a chemokine receptor in monotherapy will offer therapeutic benefit. A similar role of multiple chemokines have been shown to be correlated with clinical stage of disease in diabetic retinopathy and dry eye (Meleth et al., 2005; Yamagami et al., 2005). In these ocular diseases the use of broad spectrum chemokine receptor inhibitor which inhibits the function of a wide range of chemokines may be beneficial.

The first broad spectrum chemokine inhibitor (BSCI) to be reported was termed Peptide 3, which was derived from the sequence of human chemokine MCP-1 and was shown to block the migration of monocytes in response to MCP-1, MIP-1, RANTES and SDF-1 (Reckless and Grainger. 1999). A cyclic retro inverse analogue of Peptide 3, constructed of D-amino acids in the reverse sequence, called NR58-3.14.3 was observed to be a more potent chemokine inhibitor (Beech et al., 2001). NR58-3.14.3 has been used to test for anti-inflammatory activities in animal models of atherosclerosis, lung inflammation, irritable bowel syndrome etc (Beech et al., 2001; Grainger and Reckless. 2003; Tokuyama et al., 2005). However there are several disadvantages to using these BSCI as a long-term therapeutic strategy. The known BSCIs which are peptides which have relatively low potency, poor pharmacokinetics, and are unstable in vivo. In addition, systemic use of broad spectrum chemokine receptor inhibitors could potentially lead to deleterious side effects due to their systemic anti-inflammatory activity. However in ocular diseases, a local or topical application would prevent the broad spectrum inhibitor to be taken up systemically. Identification of a small molecule inhibitor of several chemokine receptors could be very useful for treatment of inflammatory ocular diseases. Given the evidence for the role of multiple chemokines in several ocular diseases and these results, we propose that the use of small and large molecule broad spectrum chemokine receptor inhibitors will have utility in the local treatment of ocular inflammatory diseases including, but not limited to, uveitis, dry eye, diabetic retinopathy, allergic eye disease and proliferative retinopathies. Manipulation of multiple chemokines therefore represents a novel therapeutic approach in treating ocular diseases.

WO2008008374 discloses CCR2 inhibitors and methods of use thereof.

WO03/099773 discloses CCR9 inhibitors and methods of use thereof.

US2012014997 discloses CCR9 inhibitors and methods of use thereof.

U.S. Pat. No. 7,622,583 discloses heteroaryl sulfonamides as antagonists of the CCR2 receptor.

US20110118248 discloses heteroaryl sulfonamides as antagonists of the CCR2 receptor.

U.S. Pat. No. 7,884,110 discloses CCR2 inhibitors and methods of use thereof.

US 2008/0293720 discloses pyridinyl sulfonamide modulators of chemokine receptors.

U.S. Pat. No. 7,393,873 discloses arylsulfonamide derivatives.

SUMMARY OF THE INVENTION

A group of novel benzofuran-2-sulfonamide derivatives which are potent and selective chemokine receptor modulators, has been now discovered. As such, the compounds described herein are useful in treating a wide variety of disorders associated with modulation of chemokine receptors. The term "modulator" as used herein, includes but is not limited to: receptor agonist, antagonist, inverse agonist, inverse antagonist, partial agonist, partial antagonist.

This invention describes compounds of Formula I, which have chemokine receptor biological activity. The compounds in accordance with the present invention are thus of use in medicine, for example in the treatment of humans with diseases and conditions that are alleviated by chemokine receptor modulation.

In one aspect, the invention provides a compound having Formula I or a pharmaceutically acceptable salt thereof or stereoisomeric forms thereof, or the individual geometrical isomers, enantiomers, diastereoisomers, tautomers, zwitterions and pharmaceutically acceptable salts thereof:

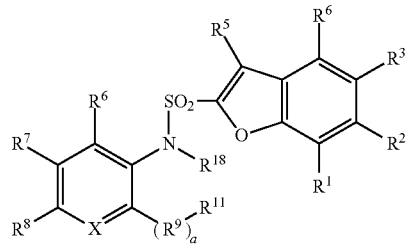

Formula I wherein:
$R^1$ is hydrogen, halogen, CN, substituted or unsubstituted $C_{1-6}$ alkyl, $OR^{12}$, $NR^{13}R^{14}$, or $COR^{15}$;
$R^2$ is hydrogen, halogen, CN, substituted or unsubstituted $C_{1-6}$ alkyl, $OR^{12}$, $NR^{13}R^{14}$, or $COR^{15}$;
$R^3$ is hydrogen, halogen, CN, substituted or unsubstituted $C_{1-6}$ alkyl, $OR^{12}$, $NR^{13}R^{14}$, or $COR^{15}$;
$R^4$ is hydrogen, halogen, CN, substituted or unsubstituted $C_{1-6}$ alkyl, $OR^{12}$, $NR^{13}R^{14}$, or $COR^{15}$;
$R^5$ is hydrogen, halogen, CN, substituted or unsubstituted $C_{1-6}$ alkyl, $OR^{12}$, $NR^{13}R^{14}$, or $COR^{15}$;
$R^6$ is hydrogen, halogen, CN, substituted or unsubstituted $C_{1-6}$ alkyl, $OR^{12}$, $NR^{13}R^{14}$, or $COR^{15}$;
$R^7$ is halogen, CN, substituted or unsubstituted $C_{1-6}$ alkyl, $OR^{12}$, $NR^{13}R^{14}$, or $COR^{15}$;
$R^8$ is hydrogen, halogen, CN, substituted or unsubstituted $C_{1-6}$ alkyl, $OR^{12}$, $NR^{13}R^{14}$, or $COR^{15}$;
$R^9$ is O, C(O), S, S(O), $S(O)_2$, or —C(=$NOR^{16}$)—;
a is 0 or 1;
$R^{11}$ is CN, substituted or unsubstituted $C_{1-6}$ alkyl, $CF_3$, $OR^{12}$, $NR^{13}R^{14}$, substituted or unsubstituted $C_{6-10}$ aryl, substituted or unsubstituted heterocycle, substituted or unsubstituted $C_{3-8}$ cycloalkyl, substituted or unsubstituted $C_{2-6}$ alkyne, substituted or unsubstituted $C_{2-6}$ alkene or $COR^{15}$;
$R^{12}$ is hydrogen or substituted or unsubstituted $C_{1-6}$ alkyl;
$R^{13}$ is hydrogen or substituted or unsubstituted $C_{1-6}$ alkyl or can form an optionally substituted heterocycle with $R^{14}$;
$R^{14}$ is hydrogen, substituted or unsubstituted $C_{1-6}$ alkyl, substituted or unsubstituted heterocycle or substituted or unsubstituted $C_{6-10}$ aryl or can form an optionally substituted heterocycle with $R^{13}$;
$R^{15}$ is hydrogen, hydroxyl, substituted or unsubstituted heterocycle, substituted or unsubstituted $C_{6-10}$ aryl or substituted or unsubstituted $C_{1-6}$ alkyl;
$R^{16}$ is hydrogen or substituted or unsubstituted $C_{1-6}$ alkyl;
X is $CR^{17}$;
$R^{17}$ is hydrogen, halogen, CN, substituted or unsubstituted $C_{1-6}$ alkyl, $OR^{12}$, $NR^{13}R^{14}$, or $COR^{15}$;
$R^{18}$ is hydrogen or substituted or unsubstituted $C_{1-6}$ alkyl;
with the provisos:
a). when $R^9$ is S, S(O) or $S(O)_2$ then $R^{11}$ is substituted or unsubstituted $C_{6-10}$ aryl, substituted or unsubstituted heterocycle, or substituted or unsubstituted $C_{3-8}$ cycloalkyl; and
the compound of Formula I is not of structure:

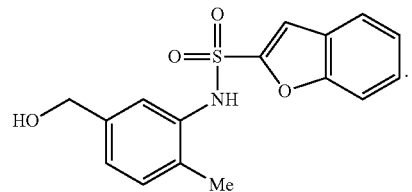 [SMILES: Cc1ccc(CO)cc1NS(=O)(=O)c1cc2ccccc2o1]

In another aspect the invention provides a compound having Formula I wherein:
$R^1$ is hydrogen;
$R^2$ is hydrogen;
$R^3$ is hydrogen;
$R^4$ is hydrogen;
$R^5$ is hydrogen;
$R^6$ is hydrogen, halogen, CN, substituted or unsubstituted $C_{1-6}$ alkyl, $OR^{12}$, $NR^{13}R^{14}$, or $COR^{15}$;
$R^7$ is halogen, CN, substituted or unsubstituted $C_{1-6}$ alkyl, $OR^{12}$, $NR^{13}R^{14}$, or $COR^{15}$;
$R^8$ is hydrogen, halogen, CN, substituted or unsubstituted $C_{1-6}$ alkyl, $OR^{12}$, $NR^{13}R^{14}$, or $COR^{15}$;
$R^9$ is S, S(O) or $S(O)_2$;
a is 1;
$R^{11}$ is substituted or unsubstituted $C_{6-10}$ aryl, substituted or unsubstituted heterocycle, substituted or unsubstituted $C_{3-8}$ cycloalkyl;
$R^{12}$ is hydrogen or substituted or unsubstituted $C_{1-6}$ alkyl;
$R^{13}$ is hydrogen or substituted or unsubstituted $C_{1-6}$ alkyl;
$R^{14}$ is hydrogen, substituted or unsubstituted $C_{1-6}$ alkyl, substituted or unsubstituted heterocycle or substituted or unsubstituted $C_{6-10}$ aryl;
$R^{15}$ is hydrogen, hydroxyl, substituted or unsubstituted heterocycle, substituted or unsubstituted $C_{6-10}$ aryl or substituted or unsubstituted $C_{1-6}$ alkyl;
$R^{16}$ is hydrogen or substituted or unsubstituted $C_{1-6}$ alkyl;
X is $CR^{17}$;
$R^{17}$ is hydrogen, halogen, CN, substituted or unsubstituted $C_{1-6}$ alkyl, $OR^{12}$, $NR^{13}R^{14}$, or $COR^{15}$;
$R^{18}$ is hydrogen or substituted or unsubstituted $C_{1-6}$ alkyl.
In another aspect the invention provides a compound having Formula I wherein:

$R^1$ is hydrogen;
$R^2$ is hydrogen;
$R^3$ is hydrogen;
$R^4$ is hydrogen;
$R^5$ is hydrogen;
$R^6$ is hydrogen, halogen, CN, substituted or unsubstituted $C_{1-6}$ alkyl, $OR^{12}$, $NR^{13}R^{14}$, or $COR^{15}$;
$R^7$ is halogen, CN, substituted or unsubstituted $C_{1-6}$ alkyl, $OR^{12}NR^{13}R^{14}$, or $COR^{15}$;
$R^8$ is hydrogen, halogen, CN, substituted or unsubstituted $C_{1-6}$ alkyl, $OR^{12}$, $NR^{13}R^{14}$, or $COR^{15}$;
$R^9$ is O or C(O);
a is 1;
$R^{11}$ is CN, substituted or unsubstituted $C_{1-6}$ alkyl, $CF_3$, $OR^{12}$, $NR^{13}R^{14}$, substituted or unsubstituted $C_{6-10}$ aryl, substituted or unsubstituted heterocycle, substituted or unsubstituted $C_{3-8}$ cycloalkyl, substituted or unsubstituted $C_{2-6}$ alkyne, substituted or unsubstituted $C_{2-6}$ alkene or $COR^{15}$;
$R^{12}$ is hydrogen or substituted or unsubstituted $C_{1-6}$ alkyl;
$R^{13}$ is hydrogen or substituted or unsubstituted $C_{1-6}$ alkyl or can form an optionally substituted heterocycle with $R^{14}$;
$R^{14}$ is hydrogen, substituted or unsubstituted $C_{1-6}$ alkyl, substituted or unsubstituted heterocycle or substituted or unsubstituted $C_{6-10}$ aryl or can form an optionally substituted heterocycle with $R^{13}$;
$R^{15}$ is hydrogen, hydroxyl, substituted or unsubstituted heterocycle, substituted or unsubstituted $C_{6-10}$ aryl or substituted or unsubstituted $C_{1-6}$ alkyl;
$R^{16}$ is hydrogen or substituted or unsubstituted $C_{1-6}$ alkyl;
X is $CR^{17}$;
$R^{17}$ is hydrogen, halogen, CN, substituted or unsubstituted $C_{1-6}$ alkyl, $OR^{12}$, $NR^{13}R^{14}$, or $COR^{15}$;
$R^{18}$ is hydrogen or substituted or unsubstituted $C_{1-6}$ alkyl.

In another aspect the invention provides a compound having Formula I wherein:
$R^1$ is hydrogen, halogen or substituted or unsubstituted $C_{1-6}$ alkyl;
$R^2$ is hydrogen, halogen or substituted or unsubstituted $C_{1-6}$ alkyl;
$R^3$ is hydrogen, halogen or substituted or unsubstituted $C_{1-6}$ alkyl;
$R^4$ is hydrogen, halogen or substituted or unsubstituted $C_{1-6}$ alkyl;
$R^5$ is hydrogen, halogen or substituted or unsubstituted $C_{1-6}$ alkyl;
$R^6$ is hydrogen, halogen or substituted or unsubstituted $C_{1-6}$ alkyl;
$R^7$ is halogen or substituted or unsubstituted $C_{1-6}$ alkyl;
$R^8$ is hydrogen, halogen or substituted or unsubstituted $C_{1-6}$ alkyl;
$R^9$ is S, S(O) or $S(O)_2$
a is 1;
$R^{11}$ is substituted or unsubstituted $C_{6-10}$ aryl, substituted or unsubstituted heterocycle or substituted or unsubstituted $C_{3-8}$ cycloalkyl;
X is $CR^{17}$;
$R^{17}$ is hydrogen; and
$R^{18}$ is hydrogen or substituted or unsubstituted $C_{1-6}$ alkyl.

In another aspect the invention provides a compound having Formula I wherein:
$R^1$ is hydrogen, halogen or substituted or unsubstituted $C_{1-6}$ alkyl;
$R^2$ is hydrogen, halogen or substituted or unsubstituted $C_{1-6}$ alkyl;
$R^3$ is hydrogen, halogen or substituted or unsubstituted $C_{1-6}$ alkyl;
$R^4$ is hydrogen, halogen or substituted or unsubstituted $C_{1-6}$ alkyl;
$R^5$ is hydrogen, halogen or substituted or unsubstituted $C_{1-6}$ alkyl;
$R^6$ is hydrogen, halogen or substituted or unsubstituted $C_{1-6}$ alkyl;
$R^7$ is halogen or substituted or unsubstituted $C_{1-6}$ alkyl;
$R^8$ is hydrogen, halogen or substituted or unsubstituted $C_{1-6}$ alkyl;
$R^9$ is O;
a is 1;
$R^{11}$ is CN, substituted or unsubstituted $C_{1-6}$ alkyl, $CF_3$, $OR^{12}$, $NR^{13}R^{14}$, substituted or unsubstituted $C_{6-10}$ aryl, substituted or unsubstituted heterocycle, substituted or unsubstituted $C_{3-8}$ cycloalkyl, substituted or unsubstituted $C_{2-6}$ alkyne, substituted or unsubstituted $C_{2-6}$ alkene or $COR^{15}$;
$R^{12}$ is hydrogen or substituted or unsubstituted $C_{1-6}$ alkyl;
$R^{13}$ is hydrogen or substituted or unsubstituted $C_{1-6}$ alkyl or can form an optionally substituted heterocycle with $R^{14}$;
$R^{14}$ is hydrogen, substituted or unsubstituted $C_{1-6}$ alkyl, substituted or unsubstituted heterocycle or substituted or unsubstituted $C_{6-10}$ aryl or can form an optionally substituted heterocycle with $R^{13}$;
$R^{15}$ is hydrogen, hydroxyl, substituted or unsubstituted heterocycle, substituted or unsubstituted $C_{6-10}$ aryl or substituted or unsubstituted $C_{1-6}$ alkyl;
X is $CR^{17}$;
$R^{17}$ is hydrogen; and
$R^{18}$ is hydrogen or substituted or unsubstituted $C_{1-6}$ alkyl.

In another aspect the invention provides a compound having Formula I wherein:
$R^1$ is hydrogen, halogen or substituted or unsubstituted $C_{1-6}$ alkyl;
$R^2$ is hydrogen, halogen or substituted or unsubstituted $C_{1-6}$ alkyl;
$R^3$ is hydrogen, halogen or substituted or unsubstituted $C_{1-6}$ alkyl;
$R^4$ is hydrogen, halogen or substituted or unsubstituted $C_{1-6}$ alkyl;
$R^5$ is hydrogen, halogen or substituted or unsubstituted $C_{1-6}$ alkyl;
$R^6$ is hydrogen, halogen or substituted or unsubstituted $C_{1-6}$ alkyl;
$R^7$ is halogen;
$R^8$ is hydrogen, halogen or substituted or unsubstituted $C_{1-6}$ alkyl;
$R^9$ is C(O);
a is 1;
$R^{11}$ is CN, substituted or unsubstituted $C_{1-6}$ alkyl, $CF_3$, $OR^{12}$, $NR^{13}R^{14}$, substituted or unsubstituted $C_{6-10}$ aryl, substituted or unsubstituted heterocycle, substituted or unsubstituted $C_{3-8}$ cycloalkyl, substituted or unsubstituted $C_{2-6}$ alkyne, substituted or unsubstituted $C_{2-6}$ alkene or $COR^{15}$;
$R^{12}$ is hydrogen or substituted or unsubstituted $C_{1-6}$ alkyl;
$R^{13}$ is hydrogen or substituted or unsubstituted $C_{1-6}$ alkyl or can form an optionally substituted heterocycle with $R^{14}$;
$R^{14}$ is hydrogen, substituted or unsubstituted $C_{1-6}$ alkyl, substituted or unsubstituted heterocycle or substituted or unsubstituted $C_{6-10}$ aryl or can form an optionally substituted heterocycle with $R^{13}$;

$R^{15}$ is hydrogen, hydroxyl, substituted or unsubstituted heterocycle, substituted or unsubstituted $C_{6-10}$ aryl or substituted or unsubstituted $C_{1-6}$ alkyl;

X is $CR^{17}$;

$R^{17}$ is hydrogen; and $R^{18}$ is hydrogen or substituted or unsubstituted $C_{1-6}$ alkyl.

In another aspect the invention provides a compound having Formula I wherein:

$R^1$ is hydrogen, halogen or substituted or unsubstituted $C_{1-6}$ alkyl;

$R^2$ is hydrogen, halogen or substituted or unsubstituted $C_{1-6}$ alkyl;

$R^3$ is hydrogen, halogen or substituted or unsubstituted $C_{1-6}$ alkyl;

$R^4$ is hydrogen, halogen or substituted or unsubstituted $C_{1-6}$ alkyl;

$R^5$ is hydrogen, halogen or substituted or unsubstituted $C_{1-6}$ alkyl;

$R^6$ is hydrogen, halogen or substituted or unsubstituted $C_{1-6}$ alkyl;

$R^7$ is halogen;

$R^8$ is hydrogen, halogen or substituted or unsubstituted $C_{1-6}$ alkyl;

$R^9$ is —C(=NOR$^{16}$)—;

a is 1;

$R^{11}$ is CN, substituted or unsubstituted $C_{1-6}$ alkyl, $CF_3$, $OR^{12}$, $NR^{13}R^{14}$, substituted or unsubstituted $C_{6-10}$ aryl, substituted or unsubstituted heterocycle, substituted or unsubstituted $C_{3-8}$ cycloalkyl, substituted or unsubstituted $C_{2-6}$ alkyne, substituted or unsubstituted $C_{2-6}$ alkene or $COR^{15}$;

$R^{12}$ is hydrogen or substituted or unsubstituted $C_{1-6}$ alkyl;

$R^{13}$ is hydrogen or substituted or unsubstituted $C_{1-6}$ alkyl or can form an optionally substituted heterocycle with $R^{14}$;

$R^{14}$ is hydrogen, substituted or unsubstituted $C_{1-6}$ alkyl, substituted or unsubstituted heterocycle or substituted or unsubstituted $C_{6-10}$ aryl or can form an optionally substituted heterocycle with $R^{13}$;

$R^{15}$ is hydrogen, hydroxyl, substituted or unsubstituted heterocycle, substituted or unsubstituted $C_{6-10}$ aryl or substituted or unsubstituted $C_{1-6}$ alkyl;

$R^{16}$ is hydrogen or substituted or unsubstituted $C_{1-6}$ alkyl;

X is $CR^{17}$;

$R^{17}$ is hydrogen; and $R^{18}$ is hydrogen or substituted or unsubstituted $C_{1-6}$ alkyl.

The term "alkyl", as used herein, refers to saturated, monovalent or divalent hydrocarbon moieties having linear or branched moieties or combinations thereof and containing 1 to 6 carbon atoms. One methylene (—CH$_2$—) group, of the alkyl can be replaced by oxygen, sulfur, sulfoxide, nitrogen, carbonyl, carboxyl, sulfonyl, or by a divalent $C_{3-6}$ cycloalkyl. Hydrogen atoms on alkyl groups can be substituted by groups including, but not limited to: halogens, —OH, $C_{3-8}$ cycloalkyl, non-aromatic heterocycles, aromatic heterocycles, —OC$_{1-6}$ alkyl, —NH$_2$, —NO$_2$, amides, carboxylic acids, ketones, ethers, esters, aldehydes, or sulfonamides.

The term "cycloalkyl", as used herein, refers to a monovalent or divalent group of 3 to 8 carbon atoms, derived from a saturated cyclic hydrocarbon. Cycloalkyl groups can be monocyclic or polycyclic. Cycloalkyl can be substituted by groups including, but not limited to: halogens, —OH, $C_{3-8}$ cycloalkyl, non-aromatic heterocycles, aromatic heterocycles, —OC$_{1-6}$ alkyl, —NH$_2$, —NO$_2$, amides, ethers, esters, carboxylic acids, aldehydes, ketones, or sulfonamides.

The term "cycloalkenyl", as used herein, refers to a monovalent or divalent group of 3 to 8 carbon atoms, derived from a saturated cycloalkyl having one or more double bonds. Cycloalkenyl groups can be monocyclic or polycyclic.

Cycloalkenyl groups can be substituted by groups including, but not limited to: halogens, —OH, $C_{3-8}$ cycloalkyl, non-aromatic heterocycles, aromatic heterocycles, —OC$_{1-6}$ alkyl, —NH$_2$, —NO$_2$, amides, ethers, esters, aldehydes, ketones, carboxylic acids, sulfonamides groups.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. $C_{2-6}$ alkenyl can be in the E or Z configuration. Alkenyl groups can be substituted by $C_{1-6}$ alkyl.

The term "alkynyl", as used herein, refers to a monovalent or divalent hydrocarbon radical having 2 to 6 carbon atoms, derived from a saturated alkyl, having at least one triple bond.

The term "heterocycle" as used herein, refers to a 3 to 10 membered ring, which can be aromatic or non-aromatic, saturated or unsaturated, containing at least one heteroatom selected from O or N or S or combinations of at least two thereof, interrupting the carbocyclic ring structure. The heterocyclic ring can be interrupted by a C=O; the S heteroatom can be oxidized. Heterocycles can be monocyclic or polycyclic. Heterocyclic ring moieties can be substituted by groups including, but not limited to: halogens, —OH, $C_{3-8}$ cycloalkyl, non-aromatic heterocycles, aromatic heterocycles, —OC$_{1-6}$ alkyl, —NH$_2$, —NO$_2$, amides, ethers, esters, aldehydes, carboxylic acids, ketones, sulfonamides groups.

The term "aryl" as used herein, refers to an organic moiety derived from an aromatic hydrocarbon consisting of a ring containing 6 to 10 carbon atoms by removal of one hydrogen. Aryl can be monocyclic or polycyclic. Aryl can be substituted by groups including, but not limited to: halogens, —OH, $C_{3-8}$ cycloalkyl, non-aromatic heterocycles, aromatic heterocycles, —OC$_{1-6}$ alkyl, —NH$_2$, —NO$_2$, amides, ethers, esters, carboxylic acids, ketones, aldehydes, sulfonamides groups.

The term "amide" as used herein, represents a group of formula "—C(O)NR$^x$R$^y$" or wherein R$^x$ and R$^y$ are the same or independently H or $C_{1-6}$ alkyl.

The term "ketone" as used herein, represents a group of formula "—C(O)R$^x$" wherein R$^x$ is $C_{1-6}$ alkyl.

The term "ester" as used herein, represents a group of formula "—C(O)OR$^x$" wherein R$^x$ is $C_{1-6}$ alkyl.

The term "ether" as used herein, represents a group of formula "—OR$^x$" wherein R$^x$ is $C_{1-6}$ alkyl.

The term "aldehyde" as used herein, represents a group of formula "—C(O)H".

The term "sulfonamide" as used herein, represents a group of formula "—S(O)$_2$NR$^x$R$^y$" wherein R$^x$ and R$^y$ are the same or independently H or $C_{1-6}$ alkyl.

The term "hydroxyl" as used herein, represents a group of formula "—OH".

The term "amino" as used herein, represents a group of formula "—NH$_2$".

The term "carbonyl" as used herein, represents a group of formula "—C(O)—".

The term "carboxyl" as used herein, represents a group of formula "—C(O)O—".

The term "sulfonyl" or the term "sulfone" as used herein, represents a group of formula "—SO$_2$—".

The term "sulfate" as used herein, represents a group of formula "—O—S(O)$_2$—O—".

The term "carboxylic acid" as used herein, represents a group of formula "—C(O)OH".

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—O—P(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom

Compounds of the invention are:
N-(5-chloro-2-methoxyphenyl)-1-benzofuran-2-sulfonamide;
N-(5-chloro-2-methylphenyl)-1-benzofuran-2-sulfonamide;
N-[5-chloro-2-(trifluoromethoxy)phenyl]-1-benzofuran-2-sulfonamide;
methyl 2-[(1-benzofuran-2-ylsulfonyl)amino]-4-chlorobenzoate;
N-(5-chloro-2-ethoxyphenyl)-1-benzofuran-2-sulfonamide;
N-(5-chloro-2-ethynylphenyl)-1-benzofuran-2-sulfonamide;
N-{5-chloro-2-[(4-oxopiperidin-1-yl)carbonyl]phenyl}-1-benzofuran-2-sulfonamide;
N-[5-chloro-2-(morpholin-4-ylcarbonyl)phenyl]-1-benzofuran-2-sulfonamide;
N-{5-chloro-2-[(2-methylpyridin-3-yl)oxy]phenyl}-1-benzofuran-2-sulfonamide;
methyl 2-{2-[(1-benzofuran-2-ylsulfonyl)amino]-4-chlorophenoxy}benzoate;
2-{2-[(1-benzofuran-2-ylsulfonyl)amino]-4-chlorophenoxy}benzoic acid;
N-[5-chloro-2-(phenylsulfanyl)phenyl]-1-benzofuran-2-sulfonamide;
N-[5-chloro-2-(phenylsulfonyl)phenyl]-1-benzofuran-2-sulfonamide;
N-[5-chloro-2-(phenylsulfinyl)phenyl]-1-benzofuran-2-sulfonamide;
2-[(1-benzofuran-2-ylsulfonyl)amino]-4-chloro-N-phenylbenzamide;
N-(5-chloro-2-cyanophenyl)-1-benzofuran-2-sulfonamide;
N-[5-chloro-2-(phenylacetyl)phenyl]-1-benzofuran-2-sulfonamide;
N-{5-chloro-2-[(1Z)-N-methoxy-2-phenylethanimidoyl]phenyl}-1-benzofuran-2-sulfonamide;
N-{5-chloro-2-[(1Z)-N-hydroxy-2-phenylethanimidoyl]phenyl}-1-benzofuran-2-sulfonamide;
N-[2-(benzyloxy)-5-chlorophenyl]-1-benzofuran-2-sulfonamide;
N-[5-chloro-2-(phenylethynyl)phenyl]-1-benzofuran-2-sulfonamide;
N-[5-chloro-2-(2-phenylethyl)phenyl]-1-benzofuran-2-sulfonamide;
N-{5-chloro-2-[(Z)-2-phenylethenyl]phenyl}-1-benzofuran-2-sulfonamide;
N-[5-methyl-2-(phenylsulfanyl)phenyl]-1-benzofuran-2-sulfonamide;
N-[5-methyl-2-(phenylsulfinyl)phenyl]-1-benzofuran-2-sulfonamide;
N-[5-methyl-2-(phenylsulfonyl)phenyl]-1-benzofuran-2-sulfonamide;
N-[5-fluoro-2-(phenylsulfanyl)phenyl]-1-benzofuran-2-sulfonamide;
N-[5-fluoro-2-(phenylsulfinyl)phenyl]-1-benzofuran-2-sulfonamide;
N-[5-fluoro-2-(phenylsulfonyl)phenyl]-1-benzofuran-2-sulfonamide;
methyl 2-({2-[(1-benzofuran-2-ylsulfonyl)amino]-4-chlorophenoxy}methyl)benzoate;
2-({2-[(1-benzofuran-2-ylsulfonyl)amino]-4-chlorophenoxy}methyl)benzoic acid;
2-({2-[(1-benzofuran-2-ylsulfonyl)amino]-4-chlorophenyl}sulfanyl)benzoic acid;
3-({2-[(1-benzofuran-2-ylsulfonyl)amino]-4-chlorophenyl}sulfanyl)benzoic acid;
4-({2-[(1-benzofuran-2-ylsulfonyl)amino]-4-chlorophenyl}sulfanyl)benzoic acid;
methyl 3-({2-[(1-benzofuran-2-ylsulfonyl)amino]-4-chlorophenoxy}methyl)benzoate;
3-({2-[(1-benzofuran-2-ylsulfonyl)amino]-4-chlorophenoxy}methyl)benzoic acid;
methyl 2-(2-{2-[(1-benzofuran-2-ylsulfonyl)amino]-4-chlorophenoxy}ethyl)benzoate;
2-(2-{2-[(1-benzofuran-2-ylsulfonyl)amino]-4-chlorophenoxy}ethyl)benzoic acid.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic acid and the like (Handbook of Pharmaceutical Salts, P. Heinrich Stahal & Camille G. Wermuth (Eds), Verlag Helvetica Chemica Acta-Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahal & Camille G. Wermuth (Eds), Verlag Helvetica Chemica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the chemokine receptors.

In another embodiment, there are provided pharmaceutical compositions including at least one compound of the invention in a pharmaceutically acceptable carrier.

In a further embodiment of the invention, there are provided methods for treating disorders associated with modulation of chemokine receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by chemokine receptor modulation.

Therapeutic utilities of chemokine receptor modulators are skin inflammatory diseases and conditions, including, but are not limited to: rosacea (dilation of the blood vessels just under the skin), sunburn, chronic sun damage, discreet erythemas, psoriasis, atopic dermatitis, menopause-associated hot flashes, hot flashes resulting from orchiecto-myatopic dermatitis, photoaging, seborrheic dermatitis, acne, allergic dermatitis, irritant dermatitis, telangiectasia (dilations of previously existing small blood vessels) of the face, rhinophyma (hypertrophy of the nose with follicular dilation), red bulbous nose, acne-like skin eruptions (may ooze or crust), burning or stinging sensation of the face, irritated and bloodshot and watery eyes, cutaneous hyperactivity with dilation of blood vessels of the skin, Lyell's syndrome, Stevens-Johnson syndrome, erythema multiforme minor, erythema multiforme major and other inflammatory skin diseases, actinic keratoses, arsenic keratoses, inflammatory and non-inflammatory acne, ichthyoses and other keratinization and hyperproliferative disorders of the skin, eczema, wound healing.

Therapeutic utilities of chemokine receptor modulators are ocular inflammatory diseases including, but not limited to, uveitis, dry eye, keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy, acute macular neuroretinopathy, central serous chorioretinopathy, cystoid macular edema, and diabetic macular edema; uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi-and Harada syndrome; vasuclar diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis.

In still another embodiment of the invention, there are provided methods for treating disorders associated with modulation of chemokine receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular inflammatory diseases including, but not limited to, uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy, acute macular neuroretinopathy, central serous chorioretinopathy, cystoid macular edema, and diabetic macular edema; uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi-and Harada syndrome; vasuclar diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigement epitheliitis.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds and their pharmaceutically-acceptable salts may be administered through different routes, including but not limited to topical eye drops, direct injection, application at the back of the eye or formulations that may further enhance the long duration of actions such as a slow releasing pellet, suspension, gel, or sustained delivery devices such as any suitable drug delivery system (DDS) known in the art. While topical administration is preferred, this compound may also be used in an intraocular implant as described in U.S. Pat. No. 7,931,909.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of chemokine receptors. Thus, in further embodiments of the invention, there are provided methods for treating a disorder associated with modulation of chemokine receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. The described benzofuran-2-sulfonamide derivatives were prepared by methods as shown in Scheme 1. Those skilled in the art will be able to routinely modify and/or adapt Scheme 1 to synthesize any compounds of the invention covered by Formula I.

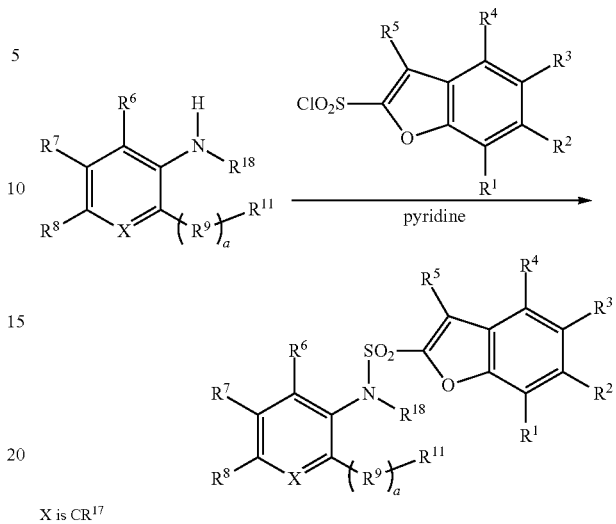

Scheme 1

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of protium $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

As will be evident to those skilled in the art, individual isomeric forms can be obtained by separation of mixtures thereof in conventional manner. For example, in the case of diastereoisomeric isomers, chromatographic separation may be employed.

Compound names were generated with ACD version 12.0 and some intermediates' and reagents' names used in the examples were generated with software such as Chem Bio Draw Ultra version 12.0 or Auto Nom 2000 from MDL ISIS Draw 2.5 SP1. In general, characterization of the compounds is performed according to the following methods:

NMR spectra are recorded on Varian 600 or Varian 300, in the indicated solvent at ambient temperature; chemical shifts in [ppm], coupling constants in [Hz].

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates were prepared according to published procedures. Solvents were purchased from commercial sources in appropriate quality and used as received. Air and/or moisture-sensitive reactions were run under an Ar— or $N_2$— atmosphere.

Usually the compounds of the invention were purified by chromatography: CombiFlash Companion and RediSep Rf silica gel 60 (0.04-0.063 mm); Preparative thin layer chromatography (PTLC): Analtech (silica gel 60 $F_{254}$, 500 or 1000 μm).

The following abbreviations are used in the examples:
$CH_2Cl_2$ dichloromethane
NaOH sodium hydroxide
MeOH methanol
$CD_3OD$ deuterated methanol
HCl hydrochloric acid
HBTU 2-(1H-Benzotriazole-1-yl)-1,1,3,3-tetramethyluronium hexafluorophosphate)
CuI copper iodide
DMF dimethylformamide
EtOAc ethyl acetate
$CDCl_3$ deuterated chloroform
$CHCl_3$ chloroform
DMSO-$d_6$ deuterated dimethyl sulfoxide
THF tetrahydrofuran
$K_2CO_3$ potassium carbonate
$N_2$ nitrogen
$Et_3N$ triethylamine
$Na_2SO_4$ sodium sulfate
$Pd(PPh_3)_2Cl_2$ Bis(triphenylphosphine)palladium(II) dichloride
$iPr_2NEt$ N,N'-diisopropylethylamine
EDC N-(3-Dimethylaminopropyl)-N'-ethylcarbodiimide hydrochloride
MPLC medium pressure liquid chromatography
$NH_4Cl$ Ammonium chloride
DMAP N,N-Dimethylpyridin-4-amine
mCPBA 3-Chloroperoxybenzoic add
$SeO_2$ Selenium dioxide
KOH potassium hydroxide
$Et_2O$ diethylether
LiBr lithium bromide
$K_2CO_3$ potassium carbonate
$TMSCHN_2$ trimethylsilyldiazomethane

EXAMPLE 1

Compound 1

N-(5-Chloro-2-methoxyphenyl)benzofuran-2-sulfonamide

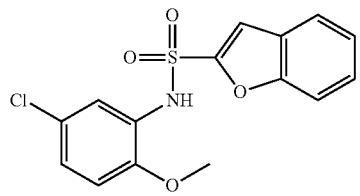 [SMILES: COc1ccc(Cl)cc1NS(=O)(=O)c1cc2ccccc2o1]

To a solution of 5-chloro-2-methoxyaniline (100 mg, 0.63 mmol) in pyridine (1 ml) at room temperature was added benzofuran-2-sulfonyl chloride (137 mg, 0.63 mmol) and the reaction was stirred during 64 hours and then was concentrated in vacuo. The residue was purified by flash column chromatography on silica gel (25% EtOAc in hexanes) to yield Compound 1 as a light yellow solid (194 mg, 91%).

$^1$H NMR (CHLOROFORM-d) δ: 7.65 (d, J=7.9 Hz, 1H), 7.59 (d, J=2.3 Hz, 1H), 7.53 (d, J=8.2 Hz, 1H), 7.46 (t, J=7.8 Hz, 1H), 7.39 (d, J=0.9 Hz, 1H), 7.30-7.34 (m, 2H), 7.02 (dd, J=8.8, 2.3 Hz, 1H), 6.68 (d, J=8.5 Hz, 1H), 3.68 (s, 3H).

EXAMPLE 2

Compound 2

N-(5-Chloro-2-methylphenyl)-1-benzofuran-2-sulfonamide

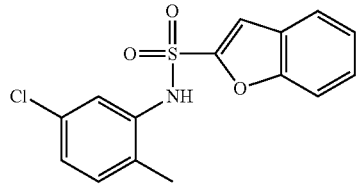 [SMILES: Cc1ccc(Cl)cc1NS(=O)(=O)c1cc2ccccc2o1]

To a solution of 5-chloro-2-methylaniline (50 μl, 0.62 mmol) in pyridine (1 ml) at room temperature was added benzofuran-2-sulfonyl chloride (135 mg, 0.62 mmol) and the reaction was stirred during 64 hours and was concentrated in vacuo. The residue was purified by flash column chromatography on silica gel (20% EtOAc in hexanes) to yield Compound 2 as a white solid (177 mg, 89%).

$^1$H NMR (CHLOROFORM-d) δ: 7.64 (d, J=7.9 Hz, 1H), 7.53 (d, J=8.5 Hz, 1H), 7.47 (ddd, J=8.4, 7.3, 1.3 Hz, 1H), 7.40 (d, J=2.1 Hz, 1H), 7.31-7.36 (m, 2H), 7.00-7.07 (m, 2H), 6.63-6.77 (m, 1H), 2.14 (s, 3H).

EXAMPLE 3

Compound 3

N-[5-Chloro-2-(trifluoromethoxy)phenyl]-1-benzofuran-2-sulfonamide

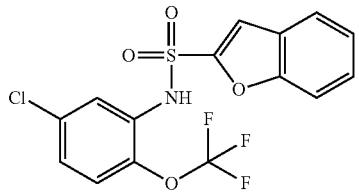 [SMILES: O=S(=O)(Nc1cc(Cl)ccc1OC(F)(F)F)c1cc2ccccc2o1]

To a solution of 5-chloro-2-(trifluoromethoxy)aniline (106 mg, 0.50 mmol) in pyridine (1 ml) at room temperature was added benzofuran-2-sulfonyl chloride (109 mg, 0.50 mmol) and the reaction was stirred during 72 hours and was concentrated in vacuo. The residue was treated with 4M NaOH (1 ml) in MeOH (3 ml) at room temperature for 30 minutes, acidified with 6M HCl, diluted with brine, and was extracted with EtOAc. The organic layer was dried over $Na_2SO_4$, and concentrated in vacuo. The residue was purified by flash column chromatography on silica gel (10% EtOAc in hexanes) to yield Compound 3 as an off-white solid (76 mg, 39%).

$^1$H NMR (CHLOROFORM-d) δ: 7.75 (d, J=2.1 Hz, 1H), 7.65 (d, J=7.9 Hz, 1H), 7.50-7.53 (m, 1H), 7.44-7.49 (m, 2H), 7.32 (t, J=7.2 Hz, 1H), 7.07-7.12 (m, 2H).

EXAMPLE 4

Compound 4

Methyl 2-[(1-benzofuran-2-ylsulfonyl)amino]-4-chlorobenzoate

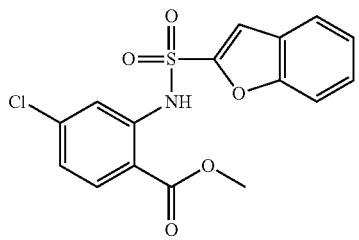 [SMILES: COC(=O)c1ccc(Cl)cc1NS(=O)(=O)c1cc2ccccc2o1]

To a solution of methyl 2-amino-4-chlorobenzoate (93 mg, 0.50 mmol) in pyridine (1 ml) at room temperature was added benzofuran-2-sulfonyl chloride (109 mg, 0.50 mmol) and the reaction was stirred for 72 hours and was concentrated in vacuo. The residue was purified by flash column chromatography on silica gel (10% EtOAc in hexanes) to yield Compound 4 as a white solid (101 mg, 55%).

$^1$H NMR (CHLOROFORM-d) δ: 11.13 (s, 1H), 7.90 (d, J=8.5 Hz, 1H), 7.84 (s, 1H), 7.69 (d, J=8.5 Hz, 1H), 7.51-7.55 (m, 2H), 7.46 (t, J=7.9 Hz, 1H), 7.31-7.36 (m, 1H), 7.05 (dd, J=8.5, 2.1 Hz, 1H), 3.92 (s, 3H).

EXAMPLE 5

Compound 5

N-(5-Chloro-2-ethoxyphenyl)-1-benzofuran-2-sulfonamide

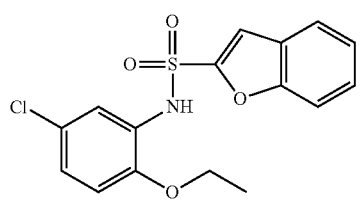 [SMILES: CCOc1ccc(Cl)cc1NS(=O)(=O)c1cc2ccccc2o1]

To a solution of 5-chloro-2-ethoxyaniline (148 mg, 0.86 mmol) in pyridine (2 ml) benzofuran-2-sulfonyl chloride (189 mg, 0.86 mmol) was added at room temperature and the reaction was stirred for 16 hours and was concentrated in vacuo. The residue was purified by flash column chromatography on silica gel (10-20% EtOAc in hexanes) to yield Compound 5 as an off-white solid (229 mg, 75%).

$^1$H NMR (CHLOROFORM-d) δ: 7.63 (d, J=7.9 Hz, 1H), 7.58 (d, J=2.3 Hz, 1H), 7.48-7.51 (m, 1H), 7.41-7.46 (m, 1H), 7.36 (s, 1H), 7.28-7.33 (m, 2H), 6.98 (dd, J=8.7, 2.5 Hz, 1H), 6.64 (d, J=8.8 Hz, 1H), 3.86 (q, J=6.8 Hz, 2H), 1.26-1.31 (m, 3H).

EXAMPLE 6

Intermediate 1

5-Chloro-2-((trimethylsilyl)ethynyl)aniline

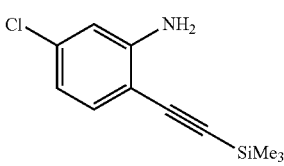 [SMILES: C[Si](C)(C)C#Cc1ccc(Cl)cc1N]

To a solution of 5-chloro-2-iodoaniline (1.50 g, 5.92 mmol) and ethynyltrimethylsilane (1.25 ml, 8.88 mmol) in $Et_3N$ (20 ml) was added CuI (5.6 mg, 0.030 mmol) and $Pd(PPh_3)_2Cl_2$ (21 mg, 0.030 mmol) and the mixture was stirred at room temperature for 5 hours. Celite was added and the suspension was filtered, rinsed with EtOAc. The filtrate was concentrated in vacuo to yield Intermediate 1 as a yellow oil (1.32 g, 100%).

$^1$H NMR (CHLOROFORM-d) δ: 7.20 (d, J=8.2 Hz, 1H), 6.69 (d, J=1.8 Hz, 1H), 6.63 (dd, J=8.2, 2.1 Hz, 1H), 4.30 (br. s., 2H), 0.27 (s, 9H).

EXAMPLE 7

Intermediate 2

N-(5-Chloro-2-((trimethylsilyl)ethynyl)phenyl)benzofuran-2-sulfonamide

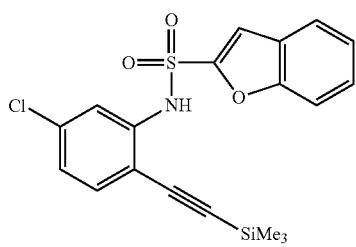 [SMILES: C[Si](C)(C)C#Cc1ccc(Cl)cc1NS(=O)(=O)c1cc2ccccc2o1]

To a solution of Intermediate 1 (1.32 g, 5.89 mmol) in pyridine (12 ml) was added benzofuran-2-sulfonyl chloride (1.53 g, 7.07 mmol) and the reaction was stirred at room temperature for 16 hours and was concentrated in vacuo. The residue was taken in EtOAc, washed with 1M HCl, brine, dried over $Na_2SO_4$, and concentrated in vacuo to yield crude Intermediate 2 as a reddish brown solid (3.5 g). The crude product was used in the next step without further purification.

EXAMPLE 8

Compound 6

N-(5-Chloro-2-ethynylphenyl)-1-benzofuran-2-sulfonamide

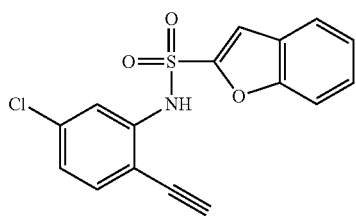 [SMILES: C#Cc1ccc(Cl)cc1NS(=O)(=O)c1cc2ccccc2o1]

To a solution of crude Intermediate 2 (3.43 g, 8.49 mmol) in MeOH (50 ml) was added $K_2CO_3$ (2.45 g, 17.8 mmol) and the mixture was stirred at room temperature for 16 hours. The solvent was removed, and the residue was acidified, extracted with EtOAc. The organic layer was washed with brine, dried over $Na_2SO_4$, and concentrated in vacuo. The crude product was purified by flash column chromatography on silica gel (0-25% EtOAc in hexanes) to yield Compound 6 as a light brown solid (1.47 g, 75%).

1H NMR (CHLOROFORM-d) δ: 7.69 (d, J=2.1 Hz, 1H), 7.68 (d, J=7.9 Hz, 1H), 7.54 (dd, J=8.5, 0.9 Hz, 1H), 7.49 (dd, J=7.0, 1.2 Hz, 2H), 7.47 (d, J=0.9 Hz, 1H), 7.32-7.37 (m, 1H), 7.31 (d, J=8.2 Hz, 1H), 7.05 (dd, J=8.2, 2.1 Hz, 1H), 3.47 (s, 1H).

EXAMPLE 9

Intermediate 3

1-(2-Amino-4-chlorobenzoyl)piperidin-4-one

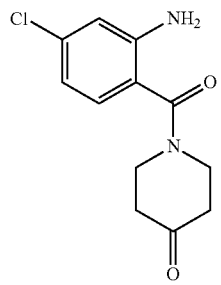 [SMILES: Nc1cc(Cl)ccc1C(=O)N1CCC(=O)CC1]

To 2-amino-4-chlorobenzoic acid (0.86 g, 5.0 mmol) and piperidin-4-one hydrochloride (0.77 g, 5.0 mmol) in DMF (10 ml) was added HBTU (1.90 g, 5.0 mmol) and $iPr_2NEt$ (2.6 ml, 15 mmol). The mixture was stirred at room temperature for 16 hours, diluted with 1M NaOH, extracted with EtOAc. The organic layer was washed with brine, dried over $Na_2SO_4$, and concentrated in vacuo. The crude product was purified by flash column chromatography on silica gel (50-75% EtOAc in hexanes) to yield Intermediate 3 as a light yellow solid (1.35 g, 100%).

1H NMR (acetone) δ: 7.18 (d, J=8.2 Hz, 1H), 6.86 (d, J=1.8 Hz, 1H), 6.64 (dd, J=8.2, 2.1 Hz, 1H), 5.30 (br. s., 2H), 3.85 (t, J=6.2 Hz, 4H), 2.48 (t, J=6.3 Hz, 4H).

EXAMPLE 10

Compound 7

N-{5-Chloro-2-[(4-oxopiperidin-1-yl)carbonyl]phenyl}-1-benzofuran-2-sulfonamide

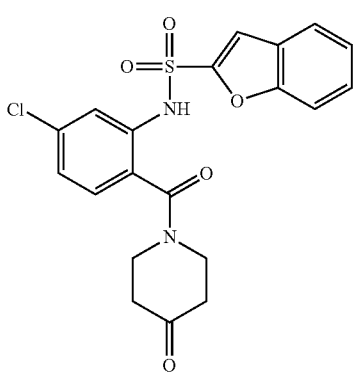 [SMILES: O=C1CCN(C(=O)c2ccc(Cl)cc2NS(=O)(=O)c2cc3ccccc3o2)CC1]

To Intermediate 3 (90 mg, 0.36 mmol) in pyridine (1.5 ml) was added benzofuran-2-sulfonyl chloride (77 mg, 0.36 mmol) and the reaction was stirred at room temperature for 6 hours and was concentrated in vacuo. The residue was purified by flash column chromatography on silica gel (50-70% EtOAc in hexanes) followed by PTLC (50% EtOAc in hexanes) to yield Compound 7 (40 mg, 26%).

1H NMR (CHLOROFORM-d) δ: 8.97 (s, 1H), 7.82 (s, 1H), 7.67 (d, J=7.9 Hz, 1H), 7.45-7.54 (m, 2H), 7.43 (s, 1H), 7.35 (t, J=7.5 Hz, 1H), 7.17 (s, 2H), 3.65 (br. s., 4H), 2.31 (br. s., 4H).

EXAMPLE 11

Intermediate 4

(2-Amino-4-chlorophenyl)(morpholino)methanone

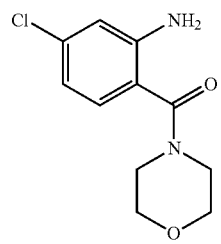 [SMILES: Nc1cc(Cl)ccc1C(=O)N1CCOCC1]

To 2-amino-4-chlorobenzoic acid (1.72 g, 10.0 mmol) and morpholine (1.3 ml, 15.0 mmol) in DMF (10 ml) was added EDC (2.30 g, 12.0 mmol). The mixture was stirred at room temperature for 16 hours, diluted with H₂O, extracted with EtOAc. The organic layer was washed with brine, dried over Na₂SO₄, and concentrated in vacuo. The crude product was purified by flash column chromatography on silica gel (50% EtOAc in hexanes) to yield Intermediate 4 as an off-white solid (2.14 g, 89%).

1H NMR (CHLOROFORM-d) δ: 7.00 (d, J=8.2 Hz, 1H), 6.66-6.75 (m, 2H), 4.49 (br. s., 2H), 3.67-3.75 (m, 4H), 3.63 (d, J=5.0 Hz, 4H).

EXAMPLE 12

Compound 8

N-[5-Chloro-2-(morpholin-4-ylcarbonyl)phenyl]-1-benzofuran-2-sulfonamide

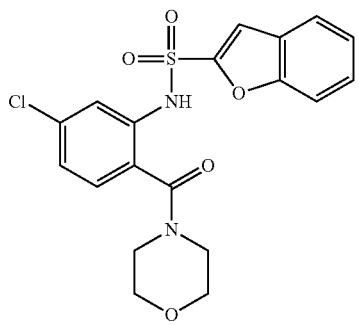 [SMILES: O=C(c1ccc(Cl)cc1NS(=O)(=O)c1cc2ccccc2o1)N1CCOCC1]

To Intermediate 4 (120 mg, 0.50 mmol) in pyridine (2 ml) was added benzofuran-2-sulfonyl chloride (108 mg, 0.50 mmol) and the reaction was stirred at room temperature for 6 hours and was concentrated in vacuo. The residue was purified by flash column chromatography on silica gel (50-70% EtOAc in hexanes) followed by PTLC (60% EtOAc in hexanes) to yield Compound 8 as an off-white solid (133 mg, 63%).

EXAMPLE 13

Intermediate 5

3-(4-Chloro-2-nitrophenoxy)-2-methylpyridine

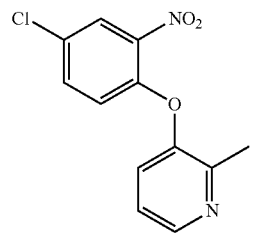

To a solution of 4-chloro-1-fluoro-2-nitrobenzene (720 mg, 4.10 mmol) in DMF (10 ml) was added 2-methylpyridin-3-ol (448 mg, 4.10 mmol) and K₂CO₃ (2.8 g, 20.5 mmol) and the reaction was stirred at 60° C. for 3 hours, diluted with H₂O, and the resulting solution was extracted with EtOAc and washed with brine, dried over Na₂SO₄ and concentrated in vacuo, followed by MPLC purification to yield Intermediate 5 as a yellow solid (1.03 g, 94%).

¹H NMR (600 MHz, acetone) δ 8.35 (d, J=4.70 Hz, 1H), 8.11 (d, J=2.64 Hz, 1H), 7.71 (dd, J=2.49, 8.95 Hz, 1H), 7.40 (d, J=8.22 Hz, 1H), 7.27 (dd, J=4.70, 8.22 Hz, 1H), 7.11 (d, J=9.10 Hz, 1H), 2.45 (s, 3H).

EXAMPLE 14

Intermediate 6

5-Chloro-2-((2-methylpyridin-3-yl)oxy)aniline

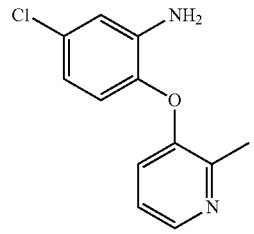 [SMILES: Cc1ncccc1Oc1ccc(Cl)cc1[N+](=O)[O-]]

To a solution of Intermediate 5 (1.03 g, 3.9 mmol) in MeOH (15 ml) was added saturated aqueous NH₄Cl (2 ml) and zinc dust (6.3 g, 98 mmol). The suspension was stirred at room temperature for 2 hour and was filtered, the filtrate was extracted with EtOAc (×2). The organic layer was washed with brine, dried over Na₂SO₄, and concentrated in vacuo. The crude Intermediate 6 (740 mg, 81%) was used in the next reaction without further purification.

¹H NMR (600 MHz, CD₃OD) δ 8.11 (d, J=4.99 Hz, 1H), 7.19 (dd, J=4.99, 8.22 Hz, 1H), 7.09 (dd, J=1.17, 8.22 Hz, 1H), 6.88 (d, J=2.35 Hz, 1H), 6.67 (d, J=8.51 Hz, 1H), 6.59 (dd, J=2.64, 8.51 Hz, 1H), 2.55 (s, 3H).

EXAMPLE 15

Compound 9

N-{5-Chloro-2-[(2-methylpyridin-3-yl)oxy]phenyl}-1-benzofuran-2-sulfonamide

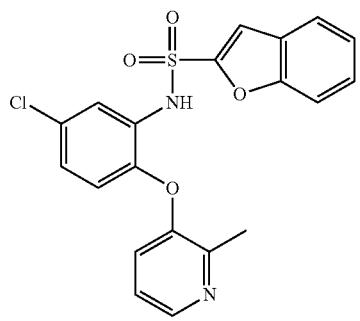 [SMILES: Cc1ncccc1Oc1ccc(Cl)cc1NS(=O)(=O)c1cc2ccccc2o1]

To Intermediate 6 (488 mg, 2.1 mmol) in pyridine (4 ml) was added benzofuran-2-sulfonyl chloride (450 mg, 2.1 mmol) and the reaction was stirred at room temperature for 16 hours. Solvent was removed in vacuo and the crude product was purified by flash column chromatography on silica gel (0-30% EtOAc in hexanes) followed by re-crystallization from 20% EtOAc/Hexane to yield Compound 9 (553 mg, 64%) as a yellow solid.

$^1$H NMR (600 MHz, CD$_3$OD) δ 8.03 (dd, J=1.17, 4.70 Hz, 1H), 7.68 (d, J=7.92 Hz, 1H), 7.63 (d, J=2.64 Hz, 1H), 7.39-7.48 (m, 2H), 7.31-7.37 (m, 2H), 7.15 (dd, J=2.64, 8.80 Hz, 1H), 6.87 (dd, J=4.69, 8.22 Hz, 1H), 6.69 (dd, J=1.17, 8.22 Hz, 1H), 6.60 (d, J=8.51 Hz, 1H), 2.20 (s, 3H).

EXAMPLE 16

Intermediate 7

Methyl 2-(4-chloro-2-nitrophenoxy)benzoate

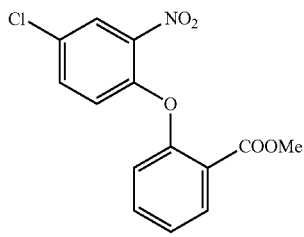 [SMILES: COC(=O)c1ccccc1Oc1ccc(Cl)cc1[N+](=O)[O-]]

To a solution of 4-chloro-1-fluoro-2-nitrobenzene (588 mg, 3.35 mmol) in DMF (10 ml) was added methyl 2-hydroxybenzoate (509 mg, 3.35 mmol) and K$_2$CO$_3$ (2.31 g, 16.75 mmol) and the reaction was stirred at 60° C. for 3 hours, diluted with H$_2$O, and the resulting solution was extracted with EtOAc and washed with brine, dried over Na$_2$SO$_4$ and concentrated in vacuo, followed by MPLC purification to yield Intermediate 7 as yellow oil (1.0 g, 99%).

$^1$H NMR (600 MHz, CD$_3$OD) δ 8.03 (d, J=2.35 Hz, 1H), 8.00 (dd, J=1.61, 7.78 Hz, 1H), 7.62-7.70 (m, 1H), 7.54 (dd, J=2.64, 9.10 Hz, 1H), 7.39 (td, J=1.17, 7.63 Hz, 1H), 7.20 (dd, J=0.88, 8.22 Hz, 1H), 6.84 (d, J=9.10 Hz, 1H), 3.74 (s, 3H).

EXAMPLE 17

Intermediate 8

Methyl 2-((3-amino-5-chloropyridin-2-yl)oxy)benzoate

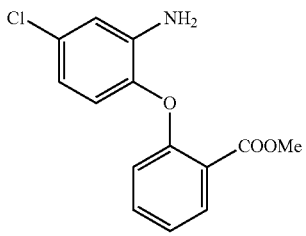 [SMILES: COC(=O)c1ccccc1Oc1ccc(Cl)cc1N]

To a solution of Intermediate 7(1.0 g, 3.26 mmol) in MeOH (30 ml) was added saturated aqueous NH$_4$Cl (2 ml) and zinc dust (5.3 g, 81 mmol). The suspension was stirred at room temperature for 1 hour and was filtered, the filtrate was extracted with EtOAc (×2). The organic layer was washed with brine, dried over Na$_2$SO$_4$, and concentrated in vacuo. The crude Intermediate 8 (770 mg, 85%) was used in the next reaction without further purification.

$^1$H NMR (600 MHz, CD$_3$OD) δ 7.82 (dd, J=1.76, 7.92 Hz, 1H), 7.43-7.50 (m, 1H), 7.12-7.18 (m, 1H), 6.90 (d, J=7.92 Hz, 1H), 6.85 (d, J=2.35 Hz, 1H), 6.70 (d, J=8.51 Hz, 1H), 6.58 (dd, J=2.20, 8.66 Hz, 1H), 3.85 (s, 3H).

EXAMPLE 18

Compound 10

Methyl 2-{2-[(1-benzofuran-2-ylsulfonyl)amino]-4-chlorophenoxy}benzoate

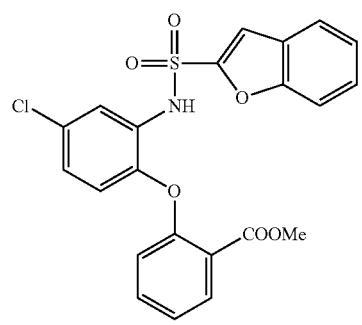 [SMILES: COC(=O)c1ccccc1Oc1ccc(Cl)cc1NS(=O)(=O)c1cc2ccccc2o1]

To Intermediate 8 (770 mg, 2.53 mmol) in pyridine (5 ml) was added benzofuran-2-sulfonyl chloride (546 mg, 2.53 mmol) and the reaction was stirred at room temperature for 16 hours. Solvent was removed in vacuo and the crude product was purified by flash column chromatography on silica gel (0-30% EtOAc in hexanes) to yield Compound 10 (920 mg, 72%) as a yellow solid.

$^1$H NMR (600 MHz, CD$_3$OD) δ 7.79 (dd, J=2.35, 7.04 Hz, 1H), 7.65-7.69 (m, 2H), 7.42-7.46 (m, 1H), 7.35-7.38

(m, 2H), 7.30-7.35 (m, 1H), 7.09 (dd, J=2.64, 8.80 Hz, 1H), 7.02-7.08 (m, 2H), 6.63 (d, J=8.51 Hz, 1H), 6.28 (dd, J=1.61, 7.78 Hz, 1H), 3.74 (s, 3H).

EXAMPLE 19

Compound 11

2-{2-[(1-Benzofuran-2-ylsulfonyl)amino]-4-chlorophenoxy}benzoic acid

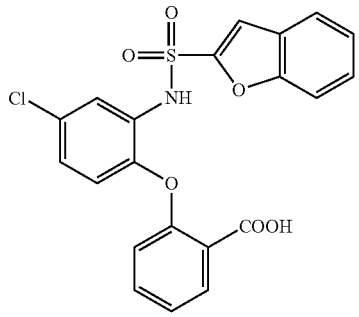 [SMILES: O=C(O)c1ccccc1Oc1ccc(Cl)cc1NS(=O)(=O)c1cc2ccccc2o1]

To Compound 10 (354 mg, 0.78 mmol) in MeOH (30 ml) was added NaOH (5M, 2 ml) and stirred at room temperature for 3 hours. The mixture was acidified with 10% HCl, extracted with EtOAc (×2). The combined organic layer was washed with brine, dried over $Na_2SO_4$, and concentrated in vacuo. The crude product was recrystallized from minimal MeOH and $CH_2Cl_2$ to yield Compound 11 (278 mg, 81%).

$^1$H NMR (600 MHz, $CD_3OD$) δ 7.81 (d, J=7.34 Hz, 1H), 7.69 (d, J=2.05 Hz, 1H), 7.65 (d, J=7.92 Hz, 1H), 7.40-7.45 (m, 1H), 7.29-7.37 (m, 3H), 7.11 (dd, J=1.76, 8.51 Hz, 1H), 6.99 (t, J=7.63 Hz, 1H), 6.89-6.95 (m, 1H), 6.72 (d, J=8.80 Hz, 1H), 6.18 (d, J=8.22 Hz, 1H).

EXAMPLE 20

Intermediate 9

(4-Chloro-2-nitrophenyl)(phenyl)sulfane

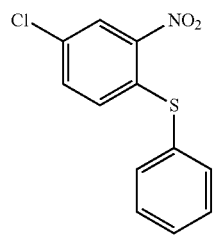 [SMILES: O=[N+]([O-])c1cc(Cl)ccc1Sc1ccccc1]

To a solution of 4-chloro-1-fluoro-2-nitrobenzene (926 mg, 5.0 mmol) in MeOH (5 ml) was added benzenethiol (0.51 ml, 5.0 mmol) and 4M NaOH (1.25 ml, 5.0 mmol) and the reaction was stirred at room temperature for 4 hours, diluted with 1M NaOH, extracted with EtOAc. The organic layer was washed with brine, dried over $Na_2SO_4$, and concentrated in vacuo. The crude product was purified by flash column chromatography on silica gel (0-5% EtOAc in hexanes) to yield Intermediate 9 as a yellow solid (1.31 g, 98%).

1H NMR (CHLOROFORM-d) δ: 8.23 (d, J=2.3 Hz, 1H), 7.56-7.61 (m, 2H), 7.48-7.53 (m, 3H), 7.30 (dd, J=8.8, 2.3 Hz, 1H), 6.80 (d, J=8.8 Hz, 1H).

EXAMPLE 21

Intermediate 10

5-Chloro-2-(phenylthio)aniline

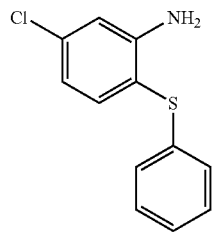 [SMILES: Nc1cc(Cl)ccc1Sc1ccccc1]

To a solution of Intermediate 9 (0.64 g, 2.4 mmol) in MeOH (20 ml) and THF (20 ml) was added saturated aqueous $NH_4Cl$ (20 ml) and zinc dust (3.95 g, 61 mmol). The suspension was stirred at room temperature for 3 hours and was filtered; the filtrate was extracted with EtOAc. The organic layer was washed with brine, dried over $Na_2SO_4$, and concentrated in vacuo. The crude product was purified by flash column chromatography on silica gel (5-10% EtOAc in hexanes) to yield Intermediate 10 as an off-white solid (555 mg, 98%).

1H NMR (CHLOROFORM-d) δ: 7.38 (d, J=8.2 Hz, 1H), 7.24 (t, J=7.6 Hz, 2H), 7.14 (t, J=7.3 Hz, 1H), 7.09 (d, J=8.2 Hz, 2H), 6.80 (d, J=2.3 Hz, 1H), 6.74 (dd, J=8.2, 2.1 Hz, 1H), 4.42 (br. s., 2H).

EXAMPLE 22

Compound 12

N-[5-Chloro-2-(phenylsulfanyl)phenyl]-1-benzofuran-2-sulfonamide

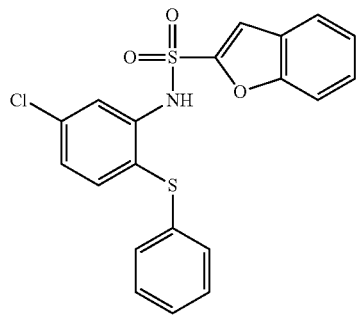 [SMILES: O=S(=O)(Nc1cc(Cl)ccc1Sc1ccccc1)c1cc2ccccc2o1]

To Intermediate 10 (394 mg, 1.67 mmol) in pyridine (5 ml) was added benzofuran-2-sulfonyl chloride (362 mg, 1.67 mmol) and the reaction was stirred at room temperature for 72 hours, when additional benzofuran-2-sulfonyl chloride (362 mg, 1.67 mmol) and catalytic amount of DMAP was added. The reaction was heated at 100° C. for 6 hours and was concentrated in vacuo. The residue was purified by flash column chromatography on silica gel (0-5% EtOAc in hexanes) to yield Compound 12 as an off-white solid (425 mg, 61%).

1H NMR (CHLOROFORM-d) δ: 8.03 (s, 1H), 7.85 (d, J=2.1 Hz, 1H), 7.66 (dt, J=8.1, 0.9 Hz, 1H), 7.39-7.48 (m, 4H), 7.31-7.37 (m, 1H), 7.04-7.11 (m, 4H), 6.89-6.93 (m, 2H).

EXAMPLE 23

Compound 13

N-[5-Chloro-2-(phenylsulfonyl)phenyl]-1-benzofuran-2-sulfonamide

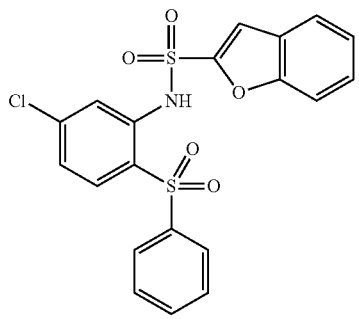 [SMILES: O=S(=O)(Nc1cc(Cl)ccc1S(=O)(=O)c1ccccc1)c1cc2ccccc2o1]

To a solution of Compound 12 (333 mg, 0.80 mmol) in CH$_2$Cl$_2$ (5 ml) was added mCPBA (208 mg, ~1.20 mmol) and the reaction was stirred at room temperature for 2 hours and was concentrated. The residue was purified by flash column chromatography on silica gel (0-50% EtOAc in hexanes) to yield Compound 13 as a white solid (204 mg, 57%).

1H NMR (CHLOROFORM-d) δ: 9.70 (s, 1H), 7.79-7.94 (m, 4H), 7.69 (d, J=7.6 Hz, 1H), 7.34-7.57 (m, 7H), 7.17 (d, J=7.9 Hz, 1H).

EXAMPLE 24

Compound 14

N-[5-Chloro-2-(phenylsulfinyl)phenyl]-1-benzofuran-2-sulfonamide

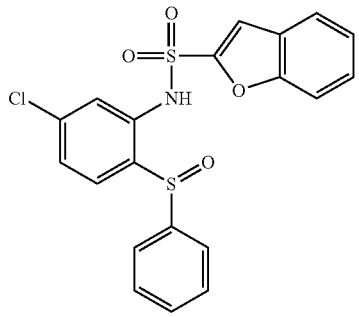 [SMILES: O=S(c1ccccc1)c1ccc(Cl)cc1NS(=O)(=O)c1cc2ccccc2o1]

To a solution of Compound 12 (333 mg, 0.80 mmol) in CH$_2$Cl$_2$ (5 ml) was added mCPBA (208 mg, ~1.20 mmol) and the reaction was stirred at room temperature for 2 hours and was concentrated. The residue was purified by flash column chromatography on silica gel (0-50% EtOAc in hexanes) to yield Compound 14 as a white solid (129 mg, 37%).

1H NMR (CHLOROFORM-d) δ: 10.66 (s, 1H), 7.78 (d, J=2.1 Hz, 1H), 7.63 (dt, J=7.9, 1.0 Hz, 1H), 7.30-7.52 (m, 10H), 7.12 (dd, J=8.2, 2.1 Hz, 1H).

EXAMPLE 25

Intermediate 11

2-Amino-4-chloro-N-phenylbenzamide

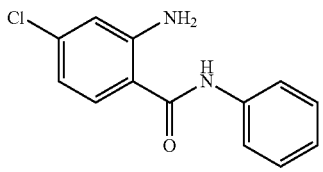 [SMILES: Nc1cc(Cl)ccc1C(=O)Nc1ccccc1]

A mixture of 4-chloro-isatoic anhydride (594 mg, 3.0 mmol), aniline (275 μl, 3.0 mmol), and NaOH (12 mg, 0.3 mmol) in dioxane (5 ml) was refluxed at 110° C. for 2 hours. The mixture was cooled to room temperature and was filtered. The filtrate was concentrated in vacuo. The residue was purified by flash column chromatography on silica gel (25% EtOAc in hexanes) to yield Intermediate 11 (200 mg, 27%).

1H NMR (CHLOROFORM-d) δ: 7.70 (br. s., 1H), 7.55 (dd, J=8.6, 1.0 Hz, 2H), 7.33-7.43 (m, 3H), 7.13-7.21 (m, 1H), 6.64-6.74 (m, 2H), 5.62 (br. s., 2H).

EXAMPLE 26

Compound 15

2-[(1-Benzofuran-2-ylsulfonyl)amino]-4-chloro-N-phenylbenzamide

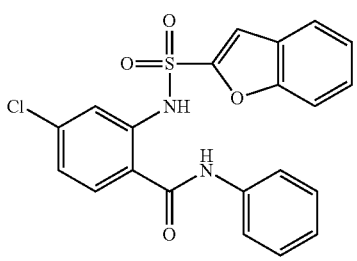 [SMILES: O=C(Nc1ccccc1)c1ccc(Cl)cc1NS(=O)(=O)c1cc2ccccc2o1]

To Intermediate 11 (200 mg, 0.81 mmol) in pyridine (2 ml) was added benzofuran-2-sulfonyl chloride (176 mg, 0.81 mmol) and a catalytic amount of DMAP. The reaction was stirred at room temperature for 6 hours, when additional benzofuran-2-sulfonyl chloride (88 mg, 0.41 mmol) was added. The reaction was continued for a total of 120 hours and was concentrated in vacuo. The crude reaction mixture was acidified with 6M HCl, extracted with EtOAc (×3). The combined organic layer was washed with brine, dried over Na$_2$SO$_4$, and concentrated in vacuo. The residue was purified by flash column chromatography on silica gel (25% EtOAc in hexanes) to yield Compound 15 as an off-white solid (135 mg, 39%).

1H NMR (CHLOROFORM-d) δ: 11.06 (s, 1H), 7.83 (d, J=2.1 Hz, 1H), 7.76 (s, 1H), 7.61 (dt, J=7.7, 1.1 Hz, 1H), 7.43-7.51 (m, 3H), 7.15-7.43 (m, 7H), 7.11 (dd, J=8.5, 2.1 Hz, 1H).

EXAMPLE 27

Compound 16

N-(5-Chloro-2-cyanophenyl)-1-benzofuran-2-sulfonamide

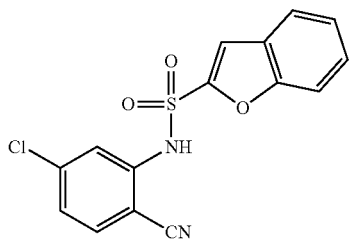 [SMILES: N#Cc1ccc(Cl)cc1NS(=O)(=O)c1cc2ccccc2o1]

To 2-amino-4-chlorobenzonitrile (552 mg, 3.62 mmol) in pyridine (5 ml) was added benzofuran-2-sulfonyl chloride (781 mg, 3.62 mmol) and the reaction was stirred at 100° C. for 16 hours, then additional benzofuran-2-sulfonyl chloride (842 mg, 3.90 mmol) was added. The reaction was continued for 24 hours and was concentrated in vacuo. The crude product was purified by flash column chromatography on silica gel (0-100% EtOAc in hexanes) to yield Compound 16 (550 mg, 36%).

$^1$H NMR (600 MHz, CD$_3$OD) δ 7.72 (dt, J=1.03, 7.92 Hz, 1H), 7.64 (d, J=8.51 Hz, 1H), 7.57-7.60 (m, 1H), 7.53 (d, J=2.05 Hz, 1H), 7.49-7.52 (m, 1H), 7.41-7.42 (m, 1H), 7.34-7.39 (m, 2H).

EXAMPLE 28

Compound 17

N-[5-Chloro-2-(phenylacetyl)phenyl]-1-benzofuran-2-sulfonamide

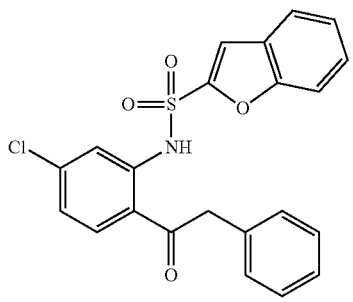 [SMILES: O=C(Cc1ccccc1)c1ccc(Cl)cc1NS(=O)(=O)c1cc2ccccc2o1]

To a solution of Compound 16 (128 mg, 0.39 mmol) in THF (2 ml) was added benzylmagnesium chloride (0.6 ml, 1.16 mmol, 2M in THF) at 0° C. After it was stirred at room temperature for 2 hours, the reaction was quenched with water, extracted with EtOAc (×2), washed with brine, dried over Na$_2$SO$_4$ and concentrated in vacuo. The crude product was purified by flash column chromatography on silica gel (0-30% EtOAc in hexanes) to yield Compound 17 (91 mg, 55%).

$^1$H NMR (600 MHz, CDCL$_3$) δ 11.95 (s, 1H), 7.82-7.91 (m, 2H), 7.66 (d, J=7.92 Hz, 1H), 7.47-7.50 (m, 2H), 7.42-7.46 (m, 1H), 7.32 (td, J=1.03, 7.41 Hz, 1H), 7.23-7.30 (m, 3H), 7.14 (d, J=7.04 Hz, 2H), 7.05 (dd, J=2.05, 8.51 Hz, 1H), 4.23 (s, 2H).

EXAMPLE 29

Compound 18

N-{5-Chloro-2-[(1Z)-N-methoxy-2-phenylethanimidoyl]phenyl}-1-benzofuran-2-sulfonamide

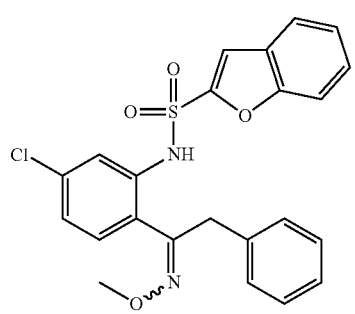 [SMILES: CON=C(Cc1ccccc1)c1ccc(Cl)cc1NS(=O)(=O)c1cc2ccccc2o1]

A mixture of Compound 17 (91 mg, 0.214 mmol), O-methylhydroxylamine hydrochloride (177 mg, 2.14 mmol) and TEA (0.8 ml) in THF (2 ml) was heated at 80° C. overnight. The reaction mixture was cooled down to room temperature, diluted with EtOAc, filtered, and the filtrate was concentrated in vacuo. The crude residue was purified by flash column chromatography on silica gel (0-30% EtOAc in hexanes) to yield Compound 18 (56 mg, 58%).

$^1$H NMR (600 MHz, CDCL$_3$) δ 11.70 (s, 1H), 7.75 (d, J=2.05 Hz, 1H), 7.63-7.67 (m, 1H), 7.49-7.53 (m, 1H), 7.43-7.48 (td, J=1.32, 7.85Hz, 1H), 7.40 (d, J=0.88 Hz, 1H), 7.33 (td, J=1.17, 7.48 Hz, 1H), 7.22 (d, J=8.80 Hz, 1H), 7.09-7.15 (m, 3H), 6.97-7.02 (m, 2H), 6.93 (dd, J=2.20, 8.66 Hz, 1H), 4.18 (s, 3H), 4.01 (s, 2H).

EXAMPLE 30

Compound 19

N-{5-Chloro-2-[(1Z)-N-hydroxy-2-phenylethanimidoyl]phenyl}-1-benzofuran-2-sulfonamide

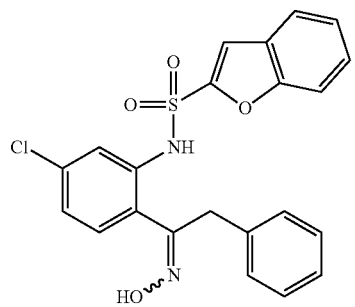 [SMILES: O=S(=O)(Nc1cc(Cl)ccc1C(Cc1ccccc1)=NO)c1cc2ccccc2o1]

The mixture of Compound 17 (121 mg, 0.28 mmol), hydroxylamine hydrochloride (198 mg, 2.80 mmol) and TEA (0.8 ml) in THF (2 ml) was heated at 80° C. overnight. The reaction mixture was cooled down to room temperature, diluted with EtOAc, filtered away salt and filtrate was concentrated in vacuo. The crude residue was purified by flash column chromatography on silica gel (0-30% EtOAc in hexanes) to yield Compound 19 (100 mg, 80%).

$^1$H NMR (600 MHz, CDCl$_3$) δ 11.40 (br. s., 1H), 7.76 (d, J=2.05 Hz, 1H), 7.66 (dt, J=1.03, 7.92 Hz, 1H), 7.50-7.53 (m, 1H), 7.45-7.48 (m, 1H), 7.43 (d, J=0.88 Hz, 1H), 7.30-7.36 (m, 1H), 7.23-7.28 (m, 1H), 7.12-7.17 (m, 3H), 7.02-7.09 (m, 2H), 6.95 (dd, J=2.05, 8.51 Hz, 1H), 4.08 (s, 2H).

EXAMPLE 31

Intermediate 12

1-(Benzyloxy)-4-chloro-2-nitrobenzene

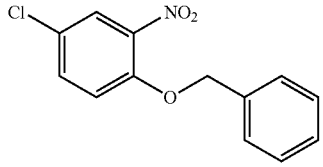

To a solution of 4-chloro-1-fluoro-2-nitrobenzene (409 mg, 2.33 mmol) in DMF (10 ml) was added phenylmethanol (0.24 ml, 2.33 mmol) and K$_2$CO$_3$ (1.6 g, 11.65 mmol) and the reaction was stirred at 60° C. for 16 hours. The reaction was diluted with H$_2$O, and the resulting solution was extracted with EtOAc and washed with brine, dried over Na$_2$SO$_4$ and concentrated in vacuo, followed by MPLC purification to yield Intermediate 12 as yellow solid (607 mg, 99%).

$^1$H NMR (600 MHz, CD$_3$OD) δ 7.86 (d, J=2.64 Hz, 1H), 7.57 (dd, J=2.79, 8.95 Hz, 1H), 7.43-7.47 (m, 2H), 7.36-7.40 (m, 2H), 7.30-7.35 (m, 2H), 5.27 (s, 2H).

EXAMPLE 32

Intermediate 13

2-(Benzyloxy)-5-chloroaniline

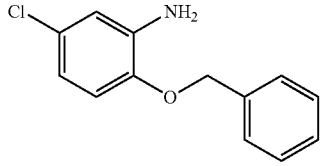 [SMILES: Nc1cc(Cl)ccc1OCc1ccccc1]

To a solution Intermediate 12 (605 mg, 2.30 mmol) in MeOH (20 ml) was added saturated aqueous NH$_4$Cl (2 ml) and zinc dust (3.7 g, 57 mmol). The suspension was stirred at room temperature for 1 hour, was filtered, and the filtrate was extracted with EtOAc (×2). The organic layer was washed with brine, dried over Na$_2$SO$_4$, and concentrated in vacuo. The crude Intermediate 13 (475 mg, 89%) was used in the next reaction without further purification.

$^1$H NMR (600 MHz, CD$_3$OD) δ 7.42-7.49 (m, 2H), 7.34-7.40 (m, 2H), 7.26-7.33 (m, 1H), 6.80 (d, J=8.80 Hz, 1H), 6.73 (d, J=2.64 Hz, 1H), 6.56 (dd, J=2.49, 8.66 Hz, 1H), 5.07 (s, 2H).

EXAMPLE 33

Compound 20

N-[2-(Benzyloxy)-5-chlorophenyl]-1-benzofuran-2-sulfonamide

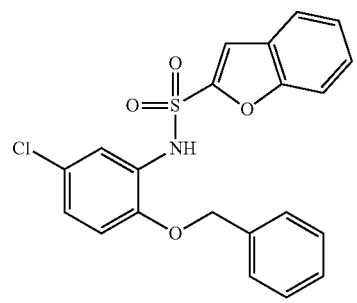 [SMILES: O=S(=O)(Nc1cc(Cl)ccc1OCc1ccccc1)c1cc2ccccc2o1]

To Intermediate 13 (233 mg, 1.0 mmol) in pyridine (3 ml) was added benzofuran-2-sulfonyl chloride (216 mg, 1.0 mmol) and the reaction was stirred at 100° C. for 16 hours. The solvent was removed in vacuo and the crude product was purified by flash column chromatography on silica gel (0-30% EtOAc in hexanes) to yield the Compound 20 (304 mg, 74%) as a yellow solid.

$^1$H NMR (600 MHz, acetone) δ 7.76 (dt, J=1.03, 7.92 Hz, 1H), 7.56 (d, J=2.64 Hz, 1H), 7.47-7.53 (m, 2H), 7.45 (d, J=0.59 Hz, 1H), 7.35-7.40 (m, 1H), 7.24-7.31 (m, 3H), 7.20-7.24 (m, 2H), 7.14 (dd, J=2.64, 8.80 Hz, 1H), 7.00 (d, J=9.10 Hz, 1H), 4.95 (s, 2H).

EXAMPLE 34

Intermediate 14

5-Chloro-2-(phenylethynyl)aniline

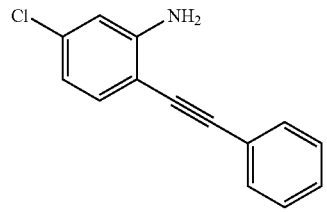 [SMILES: Nc1cc(Cl)ccc1C#Cc1ccccc1]

To 5-chloro-2-iodoaniline (1.27 g, 5.0 mmol) and ethynylbenzene (0.60 ml, 5.5 mmol) in Et$_3$N (10 ml) was added CuI (5.0 mg, 0.025 mmol) and Pd(PPh$_3$)$_2$Cl$_2$ (18 mg, 0.025 mmol) and the mixture was stirred at room temperature for 16 hours, diluted with EtOAc and was filtered through a pad of Celite. The filtrate was concentrated and the residue was purified by flash column chromatography on silica gel (0-10% EtOAc in hexanes) to yield Intermediate 14 as beige solid (1.12 g, 98%).

1H NMR (CHLOROFORM-d) δ: 7.46-7.56 (m, 2H), 7.32-7.39 (m, 3H), 7.28 (d, J=8.2 Hz, 1H), 6.66-6.75 (m, 2H), 4.37 (br. s., 2H).

EXAMPLE 35

Compound 21

N-[5-Chloro-2-(phenylethynyl)phenyl]-1-benzofuran-2-sulfonamide

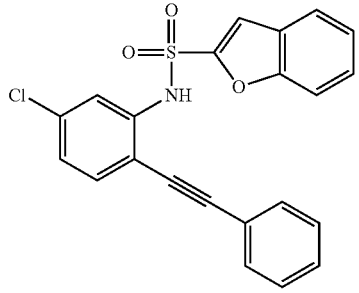 [SMILES: O=S(=O)(Nc1cc(Cl)ccc1C#Cc1ccccc1)c1cc2ccccc2o1]

To Intermediate 14 (506 mg, 2.22 mmol) in pyridine (5 ml) was added benzofuran-2-sulfonyl chloride (482 mg, 2.22 mmol) and a catalytic amount of DMAP. The reaction was stirred at room temperature for 4 hours, when additional benzofuran-2-sulfonyl chloride (121 mg, 0.56 mmol) was added. The reaction was continued for 16 hours and was concentrated in vacuo. The crude reaction mixture was acidified with 1M HCl, extracted with EtOAc (×3). The combined organic layer was washed with brine, dried over Na$_2$SO$_4$, and concentrated in vacuo. The residue was purified by flash column chromatography on silica gel (0-5% EtOAc in hexanes) to yield Compound 21 as a white solid (516 mg, 57%).

1H NMR (CHLOROFORM-d) δ: 7.71 (d, J=2.1 Hz, 1H), 7.62-7.65 (m, 1H), 7.51-7.54 (m, 2H), 7.49 (s, 1H), 7.38-7.44 (m, 5H), 7.32-7.35 (m, 2H), 7.29-7.32 (m, 1H), 7.10 (dd, J=8.2, 2.1 Hz, 1H).

EXAMPLE 36

Compound 22

N-[5-Chloro-2-(2-phenylethyl)phenyl]-1-benzofuran-2-sulfonamide

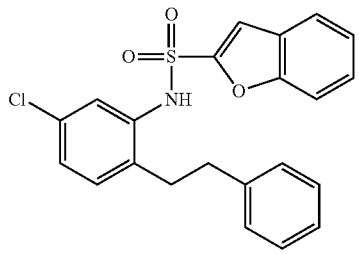 [SMILES: O=S(=O)(Nc1cc(Cl)ccc1CCc1ccccc1)c1cc2ccccc2o1]

A mixture of Compound 21 (110 mg, 0.27 mmol) and 10% palladium on activated carbon (29 mg, 0.027 mmol) in EtOAc (5 ml) was stirred at room temperature under excess hydrogen gas in a balloon for 4 hours. The mixture was filtered and the filtrate was concentrated to yield Compound 22 as off-white solid (103 mg, 93%).

1H NMR (CHLOROFORM-d) δ: 7.60-7.63 (m, 1H), 7.46-7.50 (m, 1H), 7.42-7.46 (m, 1H), 7.30-7.35 (m, 2H), 7.28 (d, J=0.9 Hz, 1H), 7.18-7.27 (m, 3H), 7.10 (dd, J=8.2, 2.3 Hz, 1H), 6.98-7.03 (m, 3H), 6.34 (s, 1H), 2.72-2.79 (m, 4H).

EXAMPLE 37

Compound 23

N-{5-Chloro-2-[((Z)-2-phenylethenyl]phenyl}-1-benzofuran-2-sulfonamide

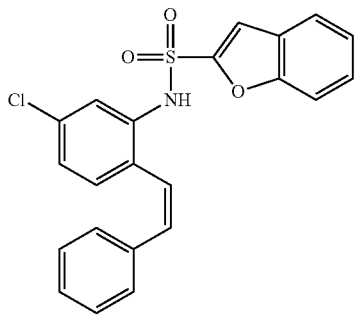 [SMILES: O=S(=O)(Nc1cc(Cl)ccc1/C=C\c1ccccc1)c1cc2ccccc2o1]

A mixture of Compound 21 (140 mg, 0.34 mmol) and 5% Lindlar's catalyst (Aldrich Lot#BCBG1137V, 144 mg, 0.068 mmol) in EtOAc (5 ml) was stirred at room temperature under excess hydrogen gas in a balloon for 4 hours. The mixture was then place under 50 psi hydrogen gas using a Parr apparatus for 3 h, and was filtered. The filtrate was concentrated and the crude product was purified by flash column chromatography on silica gel (5-10% EtOAc in hexanes) to yield Compound 23 (75 mg, 53%).

1H NMR (CHLOROFORM-d) δ: 7.61-7.66 (m, 2H), 7.42-7.48 (m, 2H), 7.30-7.36 (m, 2H), 7.11-7.16 (m, 1H), 7.06-7.11 (m, 2H), 7.01-7.06 (m, 2H), 6.94-6.98 (m, 2H), 6.87 (s, 1H), 6.72 (d, J=12.0 Hz, 1H), 6.25 (d, J=12.0 Hz, 1H).

EXAMPLE 38

Intermediate 15

(4-Methyl-2-nitrophenyl)(phenyl)sulfane

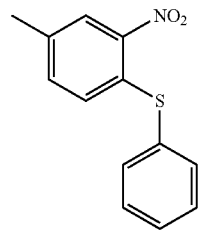 [SMILES: Cc1ccc(Sc2ccccc2)c([N+](=O)[O-])c1]

To a solution of 1-bromo-4-methyl-2-nitrobenzene (1.32 g, 6.11 mmol) in MeOH (10 ml) was added benzenethiol (0.8 ML, 6.11 mmol) and NaOH (1.5 ml, 5M) and the reaction was stirred at room temperature for 16 hours, diluted with H₂O, and the resulting solution was extracted with EtOAc and washed with brine, dried over Na₂SO₄ and concentrated in vacuo, followed by MPLC purification to yield Intermediate 15 (1.0 g, 67%).

$^1$H NMR (300 MHz, CDCl₃) δ 8.03 (d, J=1.17 Hz, 1H), 7.53-7.59 (m, 2H), 7.43-7.49 (m, 3H), 7.15 (dd, J=2.05, 8.50 Hz, 1H), 6.77 (d, J=8.20 Hz, 1H), 2.36 (s, 3H).

EXAMPLE 39

Intermediate 16

5-Methyl-2-(phenylthio)aniline

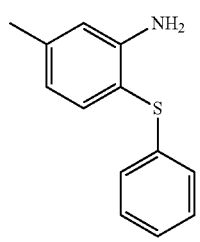

To a solution Intermediate 15 (1.0 g, 4.76 mmol) in MeOH (50 ml) was added saturated aqueous NH₄Cl (2 ml) and zinc dust (5.3 g, 82 mmol). The suspension was stirred at room temperature for 1 hour, and was filtered, and the filtrate was extracted with EtOAc (×2). The organic layer was washed with brine, dried over Na₂SO₄, and concentrated in vacuo. The crude Intermediate 16 (760 mg, 87%) was used in the next reaction without further purification.

$^1$H NMR (300 MHz, CD₃OD) δ 7.13-7.26 (m, 3H), 6.98-7.11 (m, 3H), 6.68 (d, J=0.59 Hz, 1H), 6.44-6.58 (m, 1H), 2.26 (s, 3H).

EXAMPLE 40

Compound 24

N-[5-Methyl-2-(phenylsulfanyl)phenyl]-1-benzofuran-2-sulfonamide

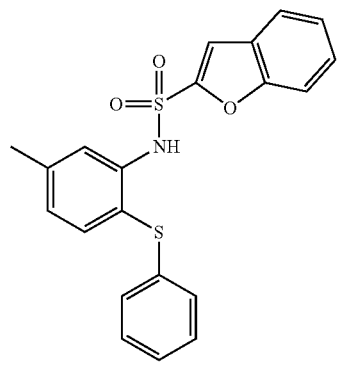 [SMILES: Cc1ccc(Sc2ccccc2)c(NS(=O)(=O)c2cc3ccccc3o2)c1]

To Intermediate 16 (335 mg, 1.56 mmol) in pyridine (5 ml) was added benzofuran-2-sulfonyl chloride (335 mg, 1.56 mmol) and the reaction was stirred at 100° C. for 4 hours, then additional benzofuran-2-sulfonyl chloride (168 mg, 0.78 mmol) was added and the reaction was stirred at 100° C. for 16 hours. 2M NaOH (2 ml) was added to the mixture, and it was heated to 100° C. for 1 hour. The mixture was diluted with water, and the products extracted with EtOAc (×2). The organic layer was washed with brine, dried over Na₂SO₄, and concentrated in vacuo. The crude product was purified by flash column chromatography on silica gel (0-30% EtOAc in hexanes) to yield Compound 24 (311 mg, 51%).

$^1$H NMR (300 MHz, CDCl₃) δ 7.99 (s, 1H), 7.57-7.67 (m, J=11.72 Hz, 2H), 7.24-7.47 (m, 4H), 6.99-7.07 (m, 3H), 6.83-6.96 (m, 3H), 2.39 (s, 3H).

EXAMPLE 41

Compound 25

N-[5-Methyl-2-(phenylsulfinyl)phenyl]-1-benzofuran-2-sulfonamide

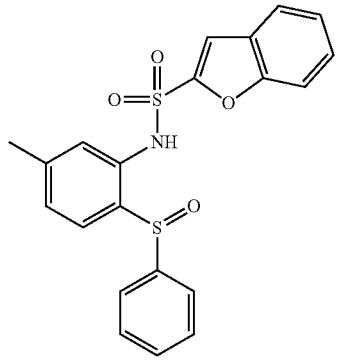 [SMILES: Cc1ccc(S(=O)c2ccccc2)c(NS(=O)(=O)c2cc3ccccc3o2)c1]

To a solution of Compound 24 (122 mg, 0.31 mmol) in CH₂Cl₂ (5 ml) was added mCPBA (62 mg, 0.31 mmol) and the reaction was stirred at 0° C. for 30 min and was concentrated. The residue was purified by flash column chromatography on silica gel (100% EtOAc) to yield Compound 25 (98 mg, 77%).

$^1$H NMR (300 MHz, CDCl₃) δ 10.48 (br. s., 1H), 7.60 (d, J=7.91 Hz, 0H), 7.55 (s, 1H), 7.50 (d, J=1.76 Hz, 1H), 7.48 (d, J=1.47 Hz, 1H), 7.38-7.44 (m, 2H), 7.23-7.37 (m, 6H), 6.95 (dd, J=0.88, 7.91 Hz, 1H), 2.35 (s, 3H).

EXAMPLE 42

Compound 26

N-[5-Methyl-2-(phenylsulfonyl)phenyl]-1-benzofuran-2-sulfonamide

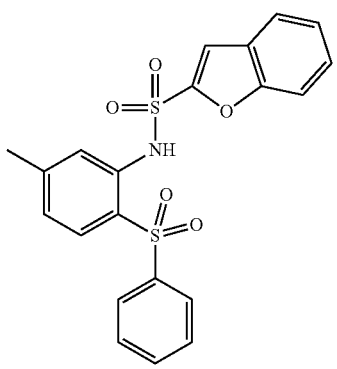 [SMILES: Cc1ccc(S(=O)(=O)c2ccccc2)c(NS(=O)(=O)c2cc3ccccc3o2)c1]

To a solution of Compound 24 (118 mg, 0.30 mmol) in CH$_2$Cl$_2$ (5 ml) was added mCPBA (150 mg, 0.75 mmol) and the reaction was stirred at room temperature for 2 hours and was concentrated. The residue was purified by flash column chromatography on silica gel (100% EtOAc) to yield Compound 26 (117 mg, 92%).

$^1$H NMR (300 MHz, CDCl$_3$) δ 7.76-7.88 (m, 3H), 7.67 (d, J=7.91 Hz, 1H), 7.58 (s, 1H), 7.26-7.53 (m, 7H), 7.02 (d, J=8.21 Hz, 1H), 2.37 (s, 3H).

EXAMPLE 43

Intermediate 17

(4-Fluoro-2-nitrophenyl)(phenyl)sulfane

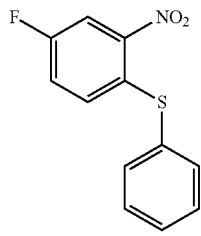 [SMILES: O=[N+]([O-])c1cc(F)ccc1Sc1ccccc1]

To a solution of 1-chloro-4-fluoro-2-nitrobenzene (1.20 g, 6.82 mmol) in MeOH (10 ml) was added benzenethiol (1.0 ML, 10.22 mmol) and NaOH (1.5 ml, 5M) and the reaction was stirred at room temperature for 16 hours, diluted with H$_2$O, and the resulting solution was extracted with EtOAc and washed with brine, dried over Na$_2$SO$_4$ and concentrated in vacuo, followed by MPLC purification to yield Intermediate 17 (1.3 g, 80%).

$^1$H NMR (300 MHz, CDCl$_3$) δ 7.94 (dd, J=2.78, 8.35 Hz, 1H), 7.54-7.63 (m, 2H), 7.44-7.52 (m, 3H), 7.03-7.18 (m, 1H), 6.86 (dd, J=4.98, 9.08 Hz, 1H).

EXAMPLE 44

Intermediate 18

5-Fluoro-2-(phenylthio)aniline

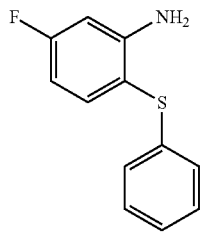 [SMILES: Nc1cc(F)ccc1Sc1ccccc1]

To a solution Intermediate 17 (1.3 g, 5.20 mmol) in MeOH (50 ml) was added saturated aqueous NH$_4$Cl (2 ml) and zinc dust (8.4 g, 130 mmol). The suspension was stirred at room temperature for 1 hour and was filtered, the filtrate was extracted with EtOAc (×2). The organic layer was washed with brine, dried over Na$_2$SO$_4$, and concentrated in vacuo. The crude Intermediate 18 (980 mg, 86%) was used in the next reaction without further purification.

$^1$H NMR (300 MHz, CDCl$_3$) δ 7.35-7.50 (m, 1H), 7.18-7.30 (m, 2H), 7.00-7.17 (m, 3H), 6.37-6.57 (m, 2H), 4.02 (br. s., 2H).

EXAMPLE 45

Compound 27

N-[5-Fluoro-2-(phenylsulfanyl)phenyl]-1-benzofuran-2-sulfonamide

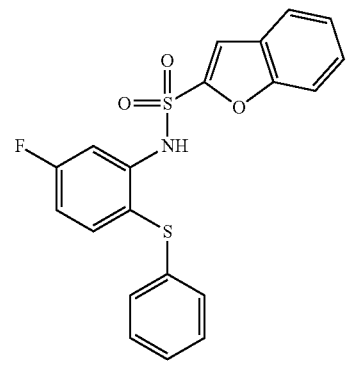 [SMILES: O=S(=O)(Nc1cc(F)ccc1Sc1ccccc1)c1cc2ccccc2o1]

To Intermediate 18 (980 mg, 4.45 mmol) in pyridine (5 ml) was added benzofuran-2-sulfonyl chloride (962 mg, 4.45 mmol) and the reaction was stirred at 100° C. for 16 hours and concentrated in vacuo. The crude product was purified by flash column chromatography on silica gel (0-30% EtOAc in hexanes) to yield Compound 27 (679 mg, 38%).

$^1$H NMR (300 MHz, CDCl$_3$) δ 8.14 (br. s, 1H), 7.56-7.67 (m, 2H), 7.29-7.54 (m, 5H), 7.00-7.08 (m, 3H), 6.78-6.90 (m, 3H).

EXAMPLE 46

Compound 28

N-[5-Fluoro-2-(phenylsulfinyl)phenyl]-1-benzofuran-2-sulfonamide

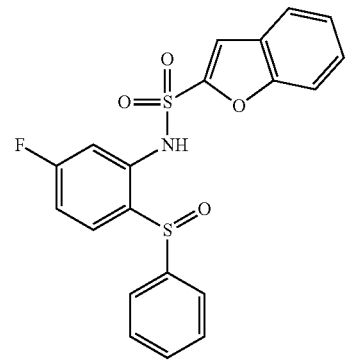 [SMILES: O=S(c1ccccc1)c1ccc(F)cc1NS(=O)(=O)c1cc2ccccc2o1]

To a solution of Compound 27 (485 mg, 0.71 mmol) in CH$_2$Cl$_2$ (5 ml) was added mCPBA (143 mg, 0.71 mmol) and the reaction was stirred at 0° C. for 30 min, and the solution was concentrated. The residue was purified by flash column chromatography on silica gel (100% EtOAc) to yield Compound 28 (420 mg, 83%).

¹H NMR (300 MHz, CDCl) δ 10.73 (br. s., 1H), 7.63 (d, J=7.91 Hz, 1H), 7.39-7.56 (m, 6H), 7.28-7.38 (m, 5H), 6.84 (td, J=2.34, 8.06 Hz, 1H).

EXAMPLE 47

Compound 29

N-[5-Fluoro-2-(phenylsulfonyl)phenyl]-1-benzofuran-2-sulfonamide

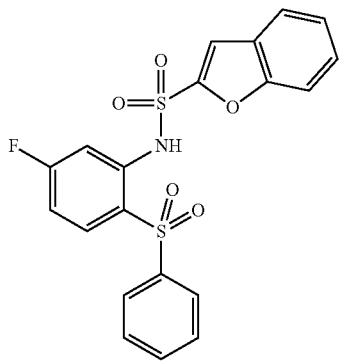 [SMILES: O=S(=O)(Nc1cc(F)ccc1S(=O)(=O)c1ccccc1)c1cc2ccccc2o1]

To a solution of Compound 27 (220 mg, 0.55 mmol) in CH₂Cl₂ (5 ml) was added mCPBA (276 mg, 1.38 mmol) and the reaction was stirred at room temperature for 2 hours and was concentrated. The residue was purified by flash column chromatography on silica gel (100% EtOAc) to yield Compound 29 (170 mg, 72%).

¹H NMR (300 MHz, CDCl₃) δ 7.97 (dd, J=6.01, 8.94 Hz, 1H), 7.78-7.89 (m, 2H), 7.68 (d, J=7.62 Hz, 1H), 7.29-7.61 (m, 8H), 6.78-6.97 (m, 1H).

EXAMPLE 48

Intermediate 19

Methyl 2-((4-Chloro-2-nitrophenoxy)methyl)benzoate

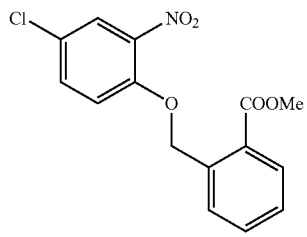 [SMILES: COC(=O)c1ccccc1COc1ccc(Cl)cc1[N+](=O)[O-]]

To a solution of 4-chloro-2-nitrophenol (541 mg, 3.12 mmol) in DMF (10 ml) was added methyl 2-(bromomethyl)benzoate (714 mg, 3.12 mmol) and K₂CO₃ (1.3 g, 9.35 mmol). The reaction was stirred at room temperature for 16 hours, diluted with H₂O, and the resulting solution was extracted with EtOAc and washed with brine, dried over Na₂SO₄ and concentrated in vacuo. The residue was purified by MPLC to yield Intermediate 19(959 mg, 96%).

¹H NMR (600 MHz, CDCl₃) δ 8.08 (dd, J=1.32, 7.78 Hz, 1H), 7.92 (d, J=2.64 Hz, 1H), 7.91 (d, J=7.92 Hz, 1H), 7.59-7.68 (m, 1H), 7.48-7.54 (m, 1H), 7.43 (t, J=7.63 Hz, 1H), 7.20 (d, J=9.10 Hz, 1H), 5.66 (s, 2H), 3.88-3.99 (m, 3H).

EXAMPLE 49

Intermediate 20

Methyl 2-((2-(Benzofuran-2-sulfonamido)-4-chlorophenoxy)methyl)benzoate

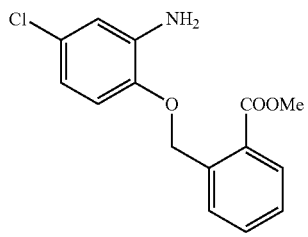 [SMILES: COC(=O)c1ccccc1COc1ccc(Cl)cc1N]

To a solution Intermediate 19 (959 mg, 2.99 mmol) in MeOH (50 ml) was added saturated aqueous NH₄Cl (2 ml) and zinc dust (3.9 g, 60 mmol). The suspension was stirred at room temperature for 1 hour, filtered, and the filtrate was extracted with EtOAc (x2). The organic layer was washed with brine, dried over Na₂SO₄, and concentrated in vacuo. The crude Intermediate 20 (713 mg, 82%) was used in the next reaction without further purification.

¹H NMR (600 MHz, CDCl₃) δ 8.01 (dd, J=1.32, 7.78 Hz, 1H), 7.61-7.66 (m, 1H), 7.55 (td, J=1.47, 7.63 Hz, 1H), 7.36-7.42 (m, 1H), 6.69-6.74 (m, 2H), 6.59-6.64 (m, 1H), 5.48 (s, 2H), 3.94 (br. s., 2H), 3.89 (s, 3H).

EXAMPLE 50

Compound 30

Methyl 2-({2-[(1-Benzofuran-2-ylsulfonyl)amino]-4-chlorophenoxy}methyl)benzoate

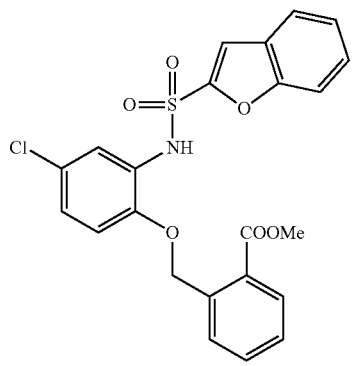 [SMILES: COC(=O)c1ccccc1COc1ccc(Cl)cc1NS(=O)(=O)c1cc2ccccc2o1]

To Intermediate 20 (329 mg, 1.13 mmol) in pyridine (5 ml) was added benzofuran-2-sulfonyl chloride (244 mg, 1.13 mmol) and the reaction was stirred at 100° C. for 16 hours and concentrated in vacuo. The crude product was purified by flash column chromatography on silica gel (0-30% EtOAc in hexanes) to yield Compound 30 (231 mg, 43%).

$^1$H NMR (600 MHz, CDCl$_3$) δ 7.99-8.07 (m, 1H), 7.58-7.67 (m, 2H), 7.51 (br. s., 1H), 7.33-7.44 (m, 4H), 7.22-7.33 (m, 3H), 6.89-7.05 (m, 1H), 6.71 (dd, J=4.70, 8.80 Hz, 1H), 5.35 (d, J=4.40 Hz, 2H), 3.89 (d, J=4.70 Hz, 3H).

EXAMPLE 51

Compound 31

2-({2-[(1-Benzofuran-2-ylsulfonyl)amino]-4-chlorophenoxy}methyl)benzoic Acid

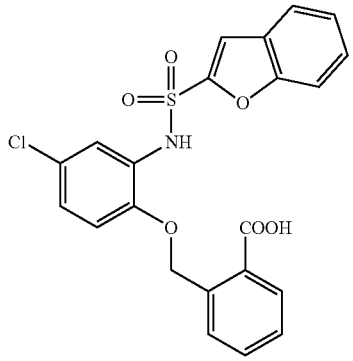 [SMILES: O=C(O)c1ccccc1COc1ccc(Cl)cc1NS(=O)(=O)c1cc2ccccc2o1]

To Compound 30 (180 mg, 0.38 mmol) in MeOH (30 ml) was added 5M NaOH (2 ml) and stirred at room temperature for 16 hours. The mixture was acidified with 10% HCl, extracted with EtOAc (×2). The combined organic layer was washed with brine, dried over Na$_2$SO$_4$, and concentrated in vacuo. The crude product was recrystallized from minimal MeOH and CH$_2$Cl$_2$ to yield Compound 31(168 mg, 96%).

$^1$H NMR (600 MHz, CDCl$_3$) δ 8.06 (dd, J=1.32, 7.78 Hz, 1H), 7.58-7.64 (m, 2H), 7.23-7.43 (m, 7H), 7.00 (dd, J=2.64, 8.80 Hz, 1H), 6.72 (d, J=8.80 Hz, 1H), 5.32 (s, 2H).

EXAMPLE 52

Intermediate 21

Methyl 2-((4-Chloro-2-nitrophenyl)thio)benzoate

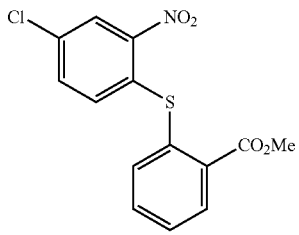 [SMILES: COC(=O)c1ccccc1Sc1ccc(Cl)cc1[N+](=O)[O-]]

To a solution of 4-chloro-1-fluoro-2-nitrobenzene (1.1 g, 6.0 mmol) in MeOH (10 ml) was added methyl 2-mercaptobenzoate (1.0 g, 6.0 mmol) and 4M NaOH (1.5 ml, 6.0 mmol) and the reaction was stirred at room temperature for 2 hours, diluted with H$_2$O, and the resulting suspension was filtered and washed with H$_2$O to yield Intermediate 21 as a yellow solid (2.0 g, crude). The crude product was used in the next reaction without further purification.

EXAMPLE 53

Intermediate 22

Methyl 2-((2-amino-4-chlorophenyl)thio)benzoate hydrochloride salt

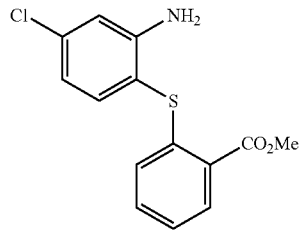

To a solution of Intermediate 21 (0.99 g, 3.1 mmol) in MeOH (15 ml) and CH$_2$Cl$_2$ (15 ml) was added saturated aqueous NH$_4$Cl (20 ml) and zinc dust (5.0 g, 77 mmol). The suspension was stirred at room temperature for 30 minutes and was filtered, the filtrate was extracted with EtOAc. The organic layer was washed with brine, dried over Na$_2$SO$_4$, and concentrated in vacuo. The crude product was dissolved in Et$_2$O, and 2M HCl in Et$_2$O (4 ml) was added. The resulting suspension was filtered and the solid was washed with Et$_2$O (×3) to yield Intermediate 22 as a white solid (0.75 g, 75%).

1H NMR (METHANOL-d4) δ: 8.01 (d, J=7.6 Hz, 1H), 7.49 (d, J=8.2 Hz, 1H), 7.31-7.41 (m, 1H), 7.20-7.28 (m, 2H), 7.15 (dd, J=8.5, 1.8 Hz, 1H), 6.78 (d, J=7.9 Hz, 1H), 3.93 (s, 3H).

EXAMPLE 54

Compound 32

2-({2-[(1-Benzofuran-2-ylsulfonyl)amino]-4-chlorophenyl}sulfanyl)benzoic Acid

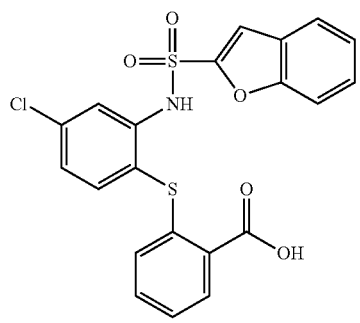 [SMILES: O=C(O)c1ccccc1Sc1ccc(Cl)cc1NS(=O)(=O)c1cc2ccccc2o1]

To Intermediate 22 (0.75 g, 2.27 mmol) in pyridine (4 ml) was added benzofuran-2-sulfonyl chloride (493 mg, 2.27 mmol) and the reaction was stirred at room temperature for 16 hours, when additional benzofuran-2-sulfonyl chloride (250 mg, 1.15 mmol) was added. The reaction was continued for 24 hours and was concentrated in vacuo. The residue was dissolved in MeOH and was treated with 4M NaOH (3 ml) at 100° C. for 15 minutes, and cooled, and acidified with 6M HCl, and the products were extracted with EtOAc (×2). The combined organic layers were washed with brine, dried over Na$_2$SO$_4$, and concentrated in vacuo. The crude product was triturated with 10% MeOH in CH$_2$Cl$_2$ to yield Compound 32 as a pinkish white solid (0.75 g, 66%).

1H NMR (acetone) δ: 11.56 (br. s., 1H), 9.21 (s, 1H), 7.99 (dd, J=7.8, 1.6 Hz, 1H), 7.88 (d, J=2.3 Hz, 1H), 7.74 (dt, J=7.9, 1.0 Hz, 1H), 7.57 (d, J=3.8 Hz, 1H), 7.56 (d, J=3.5 Hz, 1H), 7.51 (ddd, J=8.4, 7.1, 1.2 Hz, 1H), 7.45 (dd, J=8.2, 0.9 Hz, 1H), 7.37 (ddd, J=7.9, 7.0, 0.9 Hz, 1H), 7.33 (dd, J=8.2, 2.3 Hz, 1H), 7.11 (td, J=7.5, 1.2 Hz, 1H), 6.95-7.00 (m, 1H), 6.41 (dd, J=8.1, 1.0 Hz, 1H).

EXAMPLE 55

Intermediate 23

Methyl 3-((4-Chloro-2-nitrophenyl)thio)benzoate

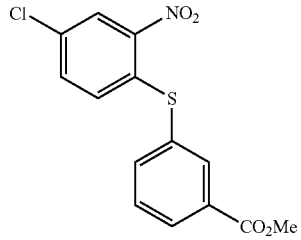

To a solution of 4-chloro-1-fluoro-2-nitrobenzene (1.0 g, 5.6 mmol) in MeOH (10 ml) was added methyl 3-mercaptobenzoate (0.95 g, 5.6 mmol) and 4M NaOH (1.4 ml, 5.6 mmol) and the reaction was stirred at room temperature for 2 hours, diluted with H$_2$O, and the resulting suspension was filtered and washed with H$_2$O to yield Intermediate 23 as a yellow solid (1.9 g, 100%).

1H NMR (CHLOROFORM-d) δ: 8.21-8.26 (m, 2H), 8.15-8.20 (m, 1H), 7.73-7.78 (m, 1H), 7.56-7.61 (m, 1H), 7.31 (dt, J=8.8, 2.1 Hz, 1H), 6.77 (dd, J=8.8, 1.8 Hz, 1H), 3.94 (s, 3H).

EXAMPLE 56

Intermediate 24

Methyl 3-((2-Amino 4-chlorophenyl)thio)benzoate

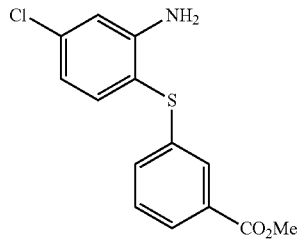 [SMILES: COC(=O)c1cccc(Sc2ccc(Cl)cc2[N+](=O)[O-])c1]

To a solution of Intermediate 23 (0.83 g, 2.6 mmol) in MeOH (15 ml) and CH$_2$Cl$_2$ (15 ml) was added saturated aqueous NH$_4$Cl (20 ml) and zinc dust (4.2 g, 64 mmol). The suspension was stirred at room temperature for 1 hour and was filtered, and the filtrate was extracted with EtOAc. The organic layer was washed with brine, dried over Na$_2$SO$_4$, and concentrated in vacuo. The crude product Intermediate 24 (0.77 g, 100%) was used in the next reaction without further purification.

1H NMR (CHLOROFORM-d) δ: 7.77-7.82 (m, 2H), 7.38 (d, J=8.2 Hz, 1H), 7.27-7.32 (m, 1H), 7.19 (ddd, J=7.9, 2.1, 1.2 Hz, 1H), 6.80 (d, J=2.3 Hz, 1H), 6.74 (dd, J=8.2, 2.1 Hz, 1H), 3.89 (s, 3H).

EXAMPLE 57

Compound 33

3-({2-[(1-Benzofuran-2-ylsulfonyl)amino]-4-chlorophenyl}sulfanyl)benzoic Acid

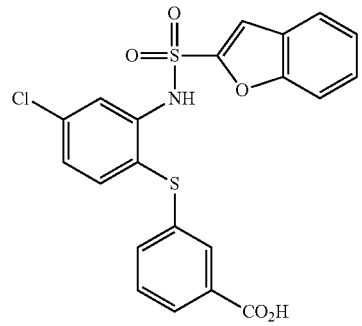 [SMILES: O=C(O)c1cccc(Sc2ccc(Cl)cc2NS(=O)(=O)c2cc3ccccc3o2)c1]

To Intermediate 24 (0.76 g, 2.6 mmol) in pyridine (4 ml) was added benzofuran-2-sulfonyl chloride (0.56 g, 2.6 mmol) and the reaction was stirred at room temperature for 16 hours, when additional benzofuran-2-sulfonyl chloride (0.28 g, 1.3 mmol) was added. The reaction was continued for 24 hours and was concentrated in vacuo. The residue was taken up in MeOH and was treated with 4M NaOH (3 ml) at 100° C. for 15 minutes, and cooled, and acidified with 6M HCl, and extracted with EtOAc (×2). The combined organic layers were washed with brine, dried over Na$_2$SO$_4$, and concentrated in vacuo. The crude product was purified by flash column chromatography on silica gel (0-50% EtOAc in hexanes) to yield Compound 33 (0.75 g, 63%).

1H NMR (acetone) δ: 7.79 (dt, J=8.0, 1.3 Hz, 1H), 7.73 (dt, J=7.9, 1.0 Hz, 1H), 7.71 (d, J=2.3 Hz, 1H), 7.69 (t, J=1.6 Hz, 1H), 7.46-7.53 (m, 3H), 7.32-7.37 (m, 2H), 7.24-7.30 (m, 2H), 7.17 (ddd, J=7.9, 2.1, 1.2 Hz, 1H).

EXAMPLE 58

Intermediate 25

Methyl 4-((4-Chloro-2-nitrophenyl)thio)benzoate

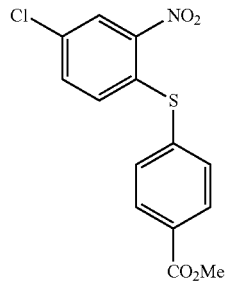 [SMILES: COC(=O)c1ccc(Sc2ccc(Cl)cc2[N+](=O)[O-])cc1]

To a solution of 4-chloro-1-fluoro-2-nitrobenzene (1.0 g, 5.6 mmol) in MeOH (10 ml) was added methyl 4-mercaptobenzoate (0.95 g, 5.6 mmol) and 4M NaOH (1.4 ml, 5.6 mmol) and the reaction was stirred at room temperature for 2 hours, diluted with H$_2$O, and the resulting suspension was filtered and washed with H$_2$O to yield Intermediate 25 As a yellow solid (1.4 g, 78%).

1H NMR (CHLOROFORM-d) δ: 8.22 (s, 1H), 8.12 (d, J=7.9 Hz, 2H), 7.63 (d, J=8.2 Hz, 2H), 7.34 (dd, J=8.8, 2.3 Hz, 1H), 6.88 (d, J=8.8 Hz, 1H), 3.97 (s, 3H).

EXAMPLE 59

Intermediate 26

Methyl 4-((2-Amino-4-chlorophenyl)thio)benzoate

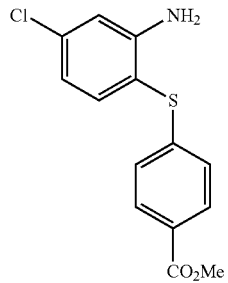 [SMILES: COC(=O)c1ccc(Sc2ccc(Cl)cc2N)cc1]

To a solution of Intermediate 25 (0.69 g, 2.1 mmol) in MeOH (15 ml) and CH$_2$Cl$_2$ (15 ml) was added saturated aqueous NH$_4$Cl (20 ml) and zinc dust (3.5 g, 54 mmol). The suspension was stirred at room temperature for 1 hour and was filtered, and the filtrate was extracted with EtOAc (×2). The organic layer was washed with brine, and dried over Na$_2$SO$_4$, and concentrated in vacuo. The crude product Intermediate 26 (0.63 g, 99%) was used in the next reaction without further purification.

1H NMR (CHLOROFORM-d) δ: 7.87 (d, J=8.5 Hz, 2H), 7.37 (d, J=8.2 Hz, 1H), 7.06 (d, J=8.5 Hz, 2H), 6.82 (d, J=2.3 Hz, 1H), 6.75 (dd, J=8.2, 2.3 Hz, 1H), 4.36 (br. s., 2H), 3.88 (s, 3H).

EXAMPLE 60

Compound 34

4-({2-[(1-Benzofuran-2-ylsulfonyl)amino]-4-chlorophenyl}sulfanyl)benzoic Acid

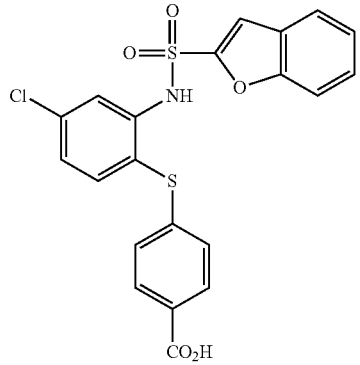 [SMILES: O=C(O)c1ccc(Sc2ccc(Cl)cc2NS(=O)(=O)c2cc3ccccc3o2)cc1]

To Intermediate 26 (0.62 g, 2.1 mmol) in pyridine (4 ml) was added benzofuran-2-sulfonyl chloride (0.46 g, 2.1 mmol) and the reaction was stirred at room temperature for 16 hours, when additional benzofuran-2-sulfonyl chloride (0.23 g, 1.1 mmol) was added. The reaction was continued for 24 hours and was concentrated in vacuo. The residue was taken up in MeOH and was treated with 4M NaOH (3 ml) at 100° C. for 15 minutes, and cooled, and acidified with 6M HCl, and the products extracted with EtOAc (×2). The combined organic layers were washed with brine, dried over Na$_2$SO$_4$, and concentrated in vacuo. The crude product was purified by flash column chromatography on silica gel (0-50% EtOAc in hexanes) followed by re-crystallization from minimal acetone and CH$_2$Cl$_2$ to yield Compound 34 (0.23 g, 24%).

1H NMR (acetone) δ: 11.17 (br. s., 1H), 9.23 (br. s., 1H), 7.78 (d, J=2.1 Hz, 1H), 7.69-7.75 (m, 3H), 7.54 (s, 1H), 7.45-7.51 (m, 3H), 7.32-7.36 (m, 2H), 6.95-6.98 (m, 2H).

EXAMPLE 61

Intermediate 27

Methyl 3-((4-Chloro-2-nitrophenoxy)methyl)benzoate

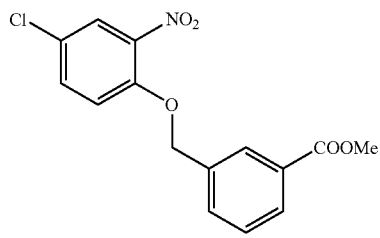 [SMILES: COC(=O)c1cccc(COc2ccc(Cl)cc2[N+](=O)[O-])c1]

To a solution of 4-chloro-2-nitrophenol (611 mg, 3.52 mmol) in DMF (10 ml) was added methyl 3-(bromomethyl)benzoate (807 mg, 3.52 mmol) and K$_2$CO$_3$ (1.46 g, 10.57 mmol) and the reaction was stirred at room temperature for 16 hours, and diluted with H$_2$O, and the resulting solution was extracted with EtOAc and washed with brine, and dried over Na$_2$SO$_4$ and concentrated in vacuo, followed by MPLC purification to yield Intermediate 27 (959 mg, 96%).

$^1$H NMR (600 MHz, CDCl$_3$) δ 8.08 (s, 1H), 8.02 (d, J=7.92 Hz, 1H), 7.87 (d, J=2.64 Hz, 1H), 7.69 (d, J=7.63 Hz, 1H), 7.46-7.51 (m, 2H), 7.06 (d, J=8.80 Hz, 1H), 5.26 (s, 2H), 3.94 (s, 3H).

EXAMPLE 62

Intermediate 28

Methyl 3-((2-(Benzofuran-2-sulfonamido)-4-chlorophenoxy)methyl)benzoate

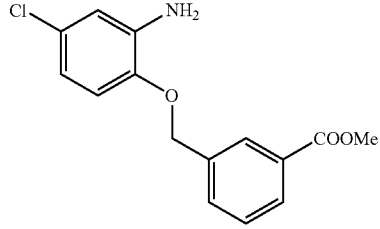 [SMILES: COC(=O)c1cccc(COc2ccc(Cl)cc2N)c1]

To a solution Intermediate 27 (630 mg, 1.96 mmol) in MeOH (20 ml) was added saturated aqueous NH$_4$Cl (2 ml) and zinc dust (2.6 g, 39 mmol). The suspension was stirred at room temperature for 1 hour and was filtered, and the filtrate was extracted with EtOAc (×2). The organic layer was washed with brine, dried over Na$_2$SO$_4$, and concentrated in vacuo. The crude Intermediate 28 (561 mg, 98%) was used in the next reaction without further purification.

$^1$H NMR (600 MHz, CDCl$_3$) δ 8.09 (dt, J=0.88, 1.76 Hz, 1H), 8.01 (d, J=7.34 Hz, 1H), 7.61 (d, J=7.63 Hz, 1H), 7.47 (t, J=7.78 Hz, 1H), 6.69-6.73 (m, 2H), 6.63 (dd, J=2.64, 8.51 Hz, 1H), 5.09 (s, 2H), 3.93 (s, 3H).

EXAMPLE 63

Compound 35

Methyl 3-({2-[(1-Benzofuran-2-ylsulfonyl)amino]-4chlorophenoxy}methyl)benzoate

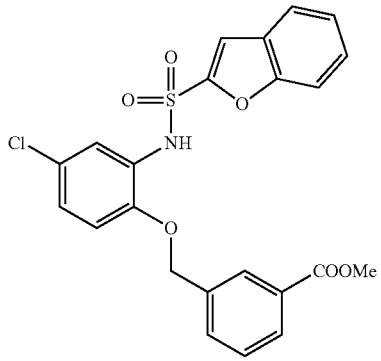 [SMILES: COC(=O)c1cccc(COc2ccc(Cl)cc2NS(=O)(=O)c2cc3ccccc3o2)c1]

To Intermediate 28 (561 mg, 1.93 mmol) in pyridine (5 ml) was added benzofuran-2-sulfonyl chloride (416 mg, 1.93 mmol) and the reaction was stirred at 100° C. for 16 hours and concentrated in vacuo. The crude product was purified by flash column chromatography on silica gel (0-30% EtOAc in hexanes) to yield Compound 35 (651 mg, 72%).

$^1$H NMR (600 MHz, CDCl$_3$) δ 8.00-8.06 (m, 1H), 7.97 (d, J=0.88 Hz, 1H), 7.60-7.67 (m, 2H), 7.42-7.49 (m, 2H), 7.36-7.40 (m, 2H), 7.28-7.35 (m, 2H), 6.99 (dd, J=2.49, 8.66 Hz, 1H), 6.72 (d, J=8.80 Hz, 1H), 4.95 (s, 2H), 3.95 (s, 3H).

EXAMPLE 64

Compound 36

3-({2-[(1-Benzofuran-2-ylsulfonyl)amino]-4-chlorophenoxy}methyl)benzoic Acid

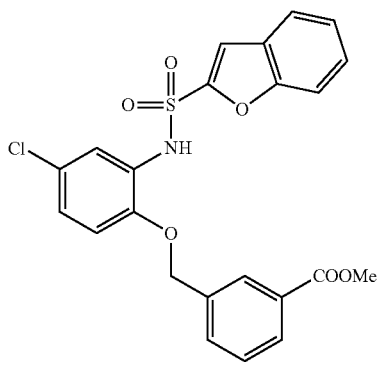 [SMILES: COC(=O)c1cccc(COc2ccc(Cl)cc2NS(=O)(=O)c2cc3ccccc3o2)c1]

To Compound 35 (506 mg, 1.07 mmol) in MeOH (30 ml) was added 5M NaOH (2 ml) and the solution stirred at room temperature for 16 hours. The mixture was acidified with 10% HCl, and extracted with EtOAc (×2). The combined organic layers were washed with brine, dried over Na$_2$SO$_4$, and concentrated in vacuo. The crude product was recrystallized from minimal MeOH and CH$_2$Cl$_2$ to yield Compound 36 (484 mg, 98%).

$^1$H NMR (600 MHz, DMSO-d$_6$) δ 13.01 (br. s., 1H), 10.57 (s, 1H), 7.78-7.84 (m, 2H), 7.62-7.67 (m, 1H), 7.42-7.47 (m, 2H), 7.37-7.42 (m, 2H), 7.31-7.35 (m, 1H), 7.27-7.31 (m, 2H), 7.24 (dd, J=2.35, 8.80 Hz, 1H), 7.00 (d, J=8.80 Hz, 1H), 4.87 (s, 2H).

EXAMPLE 65

Intermediate 29

Isochroman-1-one

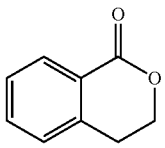 [SMILES: O=C1OCCc2ccccc21]

To isochroman (3 g, 22.4 mmol) in xylene (30 ml) was added SeO$_2$ (2.48 g, 22.4 mmol) and the mixture stirred at 140° C. for 20 hours, and then additional SeO$_2$ (2.48 g, 22.4 mmol) was added and the reaction heated for 24 hours. The mixture was cooled down to room temperature, SeO$_2$ was filtered away and xylene was removed in vacuo. The crude residue was purified by flash column chromatography on silica gel (0-20% EtOAc in hexanes) to yield Intermediate 29 (2.69g, 81%) as a pale red liquid.

$^1$H NMR (600 MHz, CDCl$_3$) δ 8.10 (dd, J=0.88, 7.63 Hz, 1H), 7.54 (td, J=1.47, 7.48 Hz, 1H), 7.37-7.41 (m, 1H), 7.24-7.28 (m, 1H), 4.51-4.55 (m, 2H), 3.06 (t, J=6.02 Hz, 2H).

EXAMPLE 66

Intermediate 30

2-(2-Hydroxyethyl)benzoic Acid

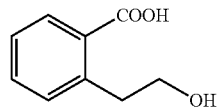 [SMILES: O=C(O)c1ccccc1CCO]

To a solution of Intermediate 29 (2.69 g, 17.97 mmol) in Et$_2$O anhydrous (50 ml) was added powdered KOH (2.01 g, 35.94 mmol), and the reaction was stirred at room temperature for 12 hours. The ether solution was decanted, the residue solid was washed with ether, then dissolved in water. The aqueous solution was acidified with 10% HCl and then extracted with ether (×3). The combine ether layers was dried over Na$_2$SO$_4$ and concentrated in vacuo to yield crude Intermediate 30 (~2 g) which was used quickly in the next step without purification.

$^1$H NMR (600 MHz, DMSO-d$_6$) δ 12.81 (br. s., 1H), 7.74 (dd, J=1.17, 7.63 Hz, 1H), 7.41-7.46 (m, 1H), 7.26-7.34 (m, 2H), 4.61 (br. s., 1H), 3.56 (t, J=7.04 Hz, 2H), 3.06 (t, J=7.04 Hz, 2H).

EXAMPLE 67

Intermediate 31

Methyl 2-(2-Hydroxyethyl)benzoate

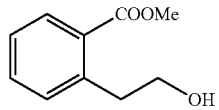 [SMILES: COC(=O)c1ccccc1CCO]

To crude Intermediate 30 (~2 g, 12.0 mmol) in anhydrous THF(12 ml) and MeOH (12 ml) under N$_2$ atmosphere at 0° C. was added TMSCHN$_2$ (7.8 ml, 15.66 mmol) via syringe until a persistent yellowish color was observed and development of gas ceased. The solvent was removed on rotary evaporator under vacuum to yield crude Intermediate 31 as a colorless oil.

EXAMPLE 68

Intermediate 32

Methyl 2-(2-(tosyloxy)ethyl)benzoate

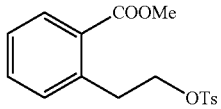 [SMILES: COC(=O)c1ccccc1CCOS(=O)(=O)c1ccc(C)cc1]

To crude Intermediate 31 in anhydrous CHCl$_3$ (25 ml) under N$_2$ atmosphere at 0° C. was added TsCl (4.5 g, 24.0 mmol) in CHCl$_3$ (10 ml) followed by addition of pyridine (3 ml, 36 mmol) immediately. The reaction was warmed up to room temperature and stirred for 12 hours, and diluted with water, and the products extracted with EtOAc. The combined organic layers were washed with brine, and dried over Na$_2$SO$_4$ and concentrated in vacuo. The residue was purified by flash column chromatography on silica gel (0-20% EtOAc in hexanes) to yield Intermediate 32 (2.2 g, 58%) as a clear oil.

$^1$H NMR (600 MHz, CDCl$_3$) δ 7.88 (dd, J=1.32, 7.78 Hz, 1H), 7.65 (d, J=8.51 Hz, 2H), 7.37-7.46 (m, 1H), 7.28-7.32 (m, 1H), 7.19-7.26 (m, 3H), 4.29 (t, J=6.60 Hz, 2H), 3.83 (s, 3H), 3.32 (t, J=6.60 Hz, 2H), 2.42 (s, 3H).

EXAMPLE 69

Intermediate 33

Methyl 2-(2-Bromoethyl)benzoate

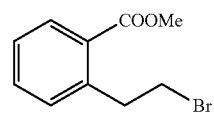 [SMILES: COC(=O)c1ccccc1CCBr]

To Intermediate 32 (1.95 g, 5.84 mmol) in acetone (10 ml) was added LiBr (1.01 g, 11.68 mmol), and the mixture was heated to reflux for 5 hours under N$_2$ atmosphere. The solvent was removed, and the residue diluted with water, and the products extracted with CH$_2$Cl$_2$. The combined organic layers were washed with brine, and dried over Na$_2$SO$_4$ and concentrated in vacuo. The crude Intermediate 33 (1.38 g) was used for next step without purification.

$^1$H NMR (600 MHz, CDCl$_3$) δ 7.96 (dd, J=1.47, 7.92 Hz, 1H), 7.44-7.51 (m, 1H), 7.28-7.37 (m, 2H), 3.91 (s, 3H), 3.64 (t, J=7.34 Hz, 2H), 3.51 (t, J=7.34 Hz, 2H).

EXAMPLE 70

Intermediate 34

Methyl 2-(2-(4-Chloro-2-nitrophenoxy)ethyl)benzoate

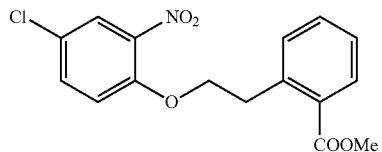 [SMILES: COC(=O)c1ccccc1CCOc1ccc(Cl)cc1[N+](=O)[O-]]

To a solution of 4-chloro-2-nitrophenol (985 mg, 5.68 mmol) in DMF (10 ml) was added crude Intermediate 33 (1.38 g, 5.68 mmol) and K$_2$CO$_3$ (3.9 g, 28.4 mmol) and the reaction was stirred at 90° C. for 16 hours, diluted with H$_2$O, and the resulting solution was extracted with EtOAc and washed with brine, dried over Na$_2$SO$_4$ and concentrated in vacuo, followed by MPLC purification to yield Intermediate 34 (520 mg, 27% for 2 steps).

$^1$H NMR (600 MHz, CDCl$_3$) δ 7.96 (dd, J=1.17, 7.92 Hz, 1H), 7.79 (d, J=2.64 Hz, 1H), 7.47-7.53 (m, 1H), 7.41-7.46 (m, 2H), 7.33 (td, J=1.17, 7.63 Hz, 1H), 7.07 (d, J=8.80 Hz, 1H), 4.39 (t, J=6.31 Hz, 2H), 3.91 (s, 3H), 3.49 (t, J=6.31 Hz, 2H).

EXAMPLE 71

Intermediate 35

Methyl 2-(2-(2-Amino-4-chlorophenoxy)ethyl)benzoate

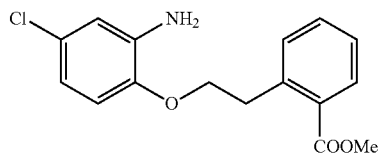 [SMILES: COC(=O)c1ccccc1CCOc1ccc(Cl)cc1N]

To a solution Intermediate 34 (685 mg, 2.04 mmol) in MeOH (20 ml) was added saturated aqueous NH$_4$Cl (2 ml) and zinc dust (3.3 g, 51 mmol). The suspension was stirred at room temperature for 1 hour and was filtered, the filtrate was extracted with EtOAc (×2). The combined organic layers were washed with brine, and dried over Na$_2$SO$_4$, and concentrated in vacuo. The crude Intermediate 35 (557 mg, 89%) was used in the next reaction without further purification.

¹H NMR (600 MHz, CDCl₃) δ 7.94 (dd, J=0.88, 7.63 Hz, 1H), 7.47 (dd, J=1.17, 7.63 Hz, 1H), 7.36 (d, J=7.63 Hz, 1H), 7.32 (td, J=1.17, 7.63 Hz, 1H), 6.69 (d, J=8.51 Hz, 1H), 6.65 (d, J=2.35 Hz, 1H), 6.60-6.64 (m, 1H), 4.23 (t, J=6.60 Hz, 2H), 3.90 (s, 3H), 3.79 (br. s., 2H), 3.49 (t, J=6.46 Hz, 2H).

EXAMPLE 72

Compound 37

Methyl 2-(2-{2-[(1-Benzofuran-2-ylsulfonyl)amino]-4chlorophenoxy}ethyl)benzoate

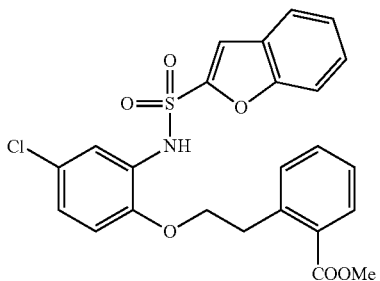 [SMILES: COC(=O)c1ccccc1CCOc1ccc(Cl)cc1NS(=O)(=O)c1cc2ccccc2o1]

To Intermediate 35 (555 mg, 1.82 mmol) in pyridine (5 ml) was added benzofuran-2-sulfonyl chloride (393 mg, 1.82 mmol) and the reaction was stirred at 100° C. for 16 hours and concentrated in vacuo. The crude product was purified by flash column chromatography on silica gel (0-30% EtOAc in hexanes) to yield Compound 37 (634 mg, 88%).

¹H NMR (600 MHz, CDCl₃) δ 7.97 (dd, J=1.17, 7.92 Hz, 1H), 7.60-7.64 (m, 1H), 7.55 (d, J=2.64 Hz, 1H), 7.53 (td, J=1.47, 7.48 Hz, 1H), 7.40-7.48 (m, 3H), 7.35 (td, J=1.17, 7.63 Hz, 1H), 7.28-7.32 (m, 2H), 6.95 (dd, J=2.49, 8.66 Hz, 1H), 6.69 (d, J=8.80 Hz, 1H), 4.13 (t, J=6.46 Hz, 2H), 3.92 (s, 3H), 3.36 (t, J=6.31 Hz, 2H).

EXAMPLE 73

Compound 38

2-(2-{2-[(1-Benzofuran-2-ylsulfonyl)amino]-4-chlorophenoxy}ethyl)benzoic Acid

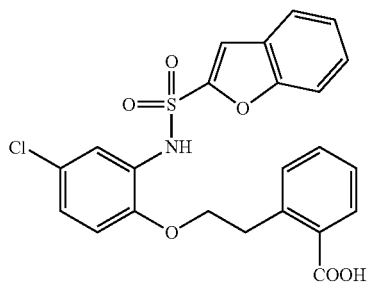 [SMILES: O=C(O)c1ccccc1CCOc1ccc(Cl)cc1NS(=O)(=O)c1cc2ccccc2o1]

To Compound 37 (505 mg, 1.04 mmol) in MeOH (30 ml) was added 5M NaOH (2 ml) and the reaction was stirred at room temperature for 16 hours. The mixture was acidified with 10% HCl, and extracted with EtOAc (×2). The combined organic layers were washed with brine, and dried over Na₂SO₄, and concentrated in vacuo. The crude product was recrystallized from minimal MeOH and CH₂Cl₂ to yield Compound 38 (454 mg, 93%).

¹H NMR (600 MHz, CDCl₃) δ 8.07 (d, J=7.92 Hz, 1H), 7.67 (br. s., 1H), 7.61 (d, J=7.92 Hz, 1H), 7.55 (td, J=1.17, 7.48 Hz, 1H), 7.52 (d, J=2.35 Hz, 1H), 7.35-7.46 (m, 3H), 7.27-7.35 (m, 3H), 6.93 (dd, J=2.49, 8.66 Hz, 1H), 6.65 (d, J=8.80 Hz, 1H), 4.10 (t, J=6.46 Hz, 2H), 3.45 (t, J=6.02 Hz, 2H).

Biological Data

HEK-Gqi5 cells stably expressing CCR2 were cultured in DMEM high glucose, 10% FBS, 1% PSA, 400 pg/ml geneticin and 50 μg/ml hygromycin. Appropriate positive control chemokines (MCP-1, MIP1A or RANTES) was used as the positive control agonist for screening compound-induced calcium activity assayed on the FLIPR$^{Tetra}$. The drug plates were prepared in 384-well microplates using the EP3 and the MultiPROBE robotic liquid handling systems. Compounds were synthesized and tested for CCR2 activity.

Table 1 shows activity: CCR2 receptor ($IC_{50}$) nM

| IUPAC Name | CCR2 IC50 (nM) | CCR2 ANTAGONISM (%) |
|---|---|---|
| N-(5-chloro-2-methoxyphenyl)-1-benzofuran-2-sulfonamide | 512 | 97 |
| N-(5-chloro-2-methylphenyl)-1-benzofuran-2-sulfonamide | 359 | 84 |
| N-[5-chloro-2-(trifluoromethoxy)phenyl]-1-benzofuran-2-sulfonamide | 195 | 95 |
| methyl 2-[(1-benzofuran-2-ylsulfonyl)amino]-4-chlorobenzoate | 1376 | 95 |
| N-(5-chloro-2-ethoxyphenyl)-1-benzofuran-2-sulfonamide | 1662 | 73 |
| N-(5-chloro-2-ethynylphenyl)-1-benzofuran-2-sulfonamide | 117 | 93 |
| N-{5-chloro-2-[(4-oxopiperidin-1-yl)carbonyl]phenyl}-1-benzofuran-2-sulfonamide | 110 | 93 |
| N-[5-chloro-2-(morpholin-4-ylcarbonyl)phenyl]-1-benzofuran-2-sulfonamide | 569 | 84 |
| N-{5-chloro-2-[(2-methylpyridin-3-yl)oxy]phenyl}-1-benzofuran-2-sulfonamide | 365 | 96 |
| methyl 2-{2-[(1-benzofuran-2-ylsulfonyl)amino]-4-chlorophenoxy}benzoate | 1018 | 98 |
| 2-{2-[(1-benzofuran-2-ylsulfonyl)amino]-4-chlorophenoxy}benzoic acid | 60 | 97 |
| N-[5-chloro-2-(phenylsulfanyl)phenyl]-1-benzofuran-2-sulfonamide | 124 | 90 |
| N-[5-chloro-2-(phenylsulfonyl)phenyl]-1-benzofuran-2-sulfonamide | 1971 | 78 |
| N-[5-chloro-2-(phenylsulfinyl)phenyl]-1-benzofuran-2-sulfonamide | 6 | 105 |
| 2-[(1-benzofuran-2-ylsulfonyl)amino]-4-chloro-N-phenylbenzamide | 328 | 95 |
| N-(5-chloro-2-cyanophenyl)-1-benzofuran-2-sulfonamide | 409 | 102 |
| N-[5-chloro-2-(phenylacetyl)phenyl]-1-benzofuran-2-sulfonamide | 183 | 79 |
| N-{5-chloro-2-[(1Z)-N-methoxy-2-phenylethanimidoyl]phenyl}-1-benzofuran-2-sulfonamide | nd | 76 |
| N-{5-chloro-2-[(1Z)-N-hydroxy-2-phenylethanimidoyl]phenyl}-1-benzofuran-2-sulfonamide | nd | 72 |
| N-[2-(benzyloxy)-5-chlorophenyl]-1-benzofuran-2-sulfonamide | 1629 | 87 |
| N-[5-chloro-2-(phenylethynyl)phenyl]-1-benzofuran-2-sulfonamide | nd | 30 |
| N-[5-chloro-2-(2-phenylethyl)phenyl]-1-benzofuran-2-sulfonamide | nd | 84 |

-continued

| IUPAC Name | CCR2 IC50 (nM) | CCR2 ANTAGONISM (%) |
|---|---|---|
| N-[5-methyl-2-(phenylsulfanyl)phenyl]-1-benzofuran-2-sulfonamide | nd | 41 |
| N-[5-methyl-2-(phenylsulfinyl)phenyl]-1-benzofuran-2-sulfonamide | 2875 | 92 |
| N-[5-methyl-2-(phenylsulfonyl)phenyl]-1-benzofuran-2-sulfonamide | nd | 38 |
| N-[5-fluoro-2-(phenylsulfanyl)phenyl]-1-benzofuran-2-sulfonamide | nd | 74 |
| N-[5-fluoro-2-(phenylsulfinyl)phenyl]-1-benzofuran-2-sulfonamide | 317 | 91 |
| N-[5-fluoro-2-(phenylsulfonyl)phenyl]-1-benzofuran-2-sulfonamide | 2618 | 82 |
| 2-({2-[(1-benzofuran-2-ylsulfonyl)amino]-4-chlorophenoxy}methyl)benzoic acid | 27 | 99 |

What is claimed is:

1. A compound represented by Formula I, its individual enantiomers, individual diastereoisomers, individual tautomers or a pharmaceutically acceptable salt thereof:

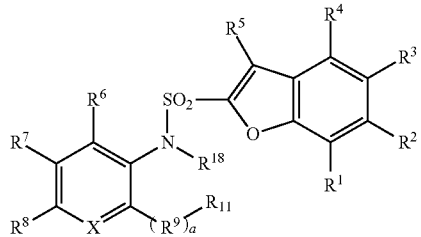

Formula I wherein:
$R^1$ to $R^6$ are hydrogen;
$R^7$ is halogen or methyl;
$R^8$ is hydrogen;
$R^9$ is O, C(O), S, S(O), S(O)$_2$ or —C(=NOR$^{16}$)—;
a is 0 or 1;
$R^{11}$ is selected from the group consisting of: -Me, —OMe, —C≡CH,

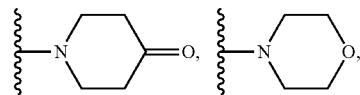

-Ph, —NHPh, —CN, —CH$_2$Ph, —C≡CPh, —CH$_2$CH$_2$Ph, —CH=CHPh,

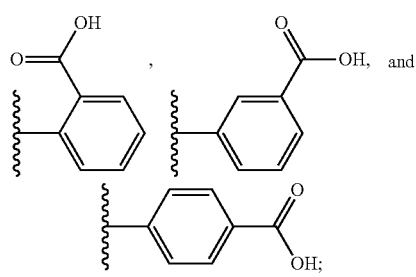

$R^{16}$ is hydrogen or methyl;
X is CH;
$R^{18}$ is hydrogen.

2. A compound according to claim 1 selected from the group consisting of:
N-(5-chloro-2-methylphenyl)-1-benzofuran-2-sulfonamide;
methyl 2-[(1-benzofuran-2-ylsulfonyl)amino]-4-chlorobenzoate;
N-(5-chloro-2-ethynylphenyl)-1-benzofuran-2-sulfonamide;
N-{5-chloro-2-[(4-oxopiperidin-1-yl)carbonyl]phenyl}-1-benzofuran-2-sulfonamide;
N-[5-chloro-2-(morpholin-4-ylcarbonyl)phenyl]-1-benzofuran-2-sulfonamide;
N-[5-chloro-2-(phenylsulfanyl)phenyl]-1-benzofuran-2-sulfonamide;
N-[5-chloro-2-(phenylsulfonyl)phenyl]-1-benzofuran-2-sulfonamide;
N-[5-chloro-2-(phenylsulfinyl)phenyl]-1-benzofuran-2-sulfonamide;
2-[(1-benzofuran-2-ylsulfonyl)amino]-4-chloro-N-phenylbenzamide;
N-(5-chloro-2-cyanophenyl)-1-benzofuran-2-sulfonamide;
N-[5-chloro-2-(phenylacetyl)phenyl]-1-benzofuran-2-sulfonamide;
N-{5-chloro-2-[(1Z)-N-methoxy-2-phenylethanimidoyl]phenyl}-1-benzofuran-2-sulfonamide;
N-{5-chloro-2-[(1Z)-N-hydroxy-2-phenylethanimidoyl]phenyl}-1-benzofuran-2-sulfonamide;
N-[5-chloro-2-(phenylethynyl)phenyl]-1-benzofuran-2-sulfonamide;
N-[5-chloro-2-(2-phenylethyl)phenyl]-1-benzofuran-2-sulfonamide;
N-{5-chloro-2-[(Z)-2-phenylethenyl]phenyl}-1-benzofuran-2-sulfonamide;
N-[5-methyl-2-(phenylsulfanyl)phenyl]-1-benzofuran-2-sulfonamide;
N-[5-methyl-2-(phenylsulfinyl)phenyl]-1-benzofuran-2-sulfonamide;
N-[5-methyl-2-(phenylsulfonyl)phenyl]-1-benzofuran-2-sulfonamide;
N-[5-fluoro-2-(phenylsulfanyl)phenyl]-1-benzofuran-2-sulfonamide;
N-[5-fluoro-2-(phenylsulfinyl)phenyl]-1-benzofuran-2-sulfonamide;
N-[5-fluoro-2-(phenylsulfonyl)phenyl]-1-benzofuran-2-sulfonamide;
2-({2-[(1-benzofuran-2-ylsulfonyl)amino]-4-chlorophenyl}sulfanyl)benzoic acid;
3-({2-[(1-benzofuran-2-ylsulfonyl)amino]-4-chlorophenyl}sulfanyl)benzoic acid; and
4-({2-[(1-benzofuran-2-ylsulfonyl)amino]-4-chlorophenyl}sulfanyl)benzoic acid.

3. A pharmaceutical composition comprising as active ingredient a therapeutically effective amount of a compound according to claim 1 and a pharmaceutically acceptable adjuvant, diluent or carrier.

4. A pharmaceutical composition according to claim 3 wherein the compound is selected from:
N-(5-chloro-2-methylphenyl)-1-benzofuran-2-sulfonamide;
methyl 2-[(1-benzofuran-2-ylsulfonyl)amino]-4-chlorobenzoate;
N-(5-chloro-2-ethynylphenyl)-1-benzofuran-2-sulfonamide;

N-{5-chloro-2-[(4-oxopiperidin-1-yl)carbonyl]phenyl}-1-benzofuran-2-sulfonamide;
N-[5-chloro-2-(morpholin-4-ylcarbonyl)phenyl]-1-benzofuran-2-sulfonamide;
N-[5-chloro-2-(phenylsulfanyl)phenyl]-1-benzofuran-2-sulfonamide;
N-[5-chloro-2-(phenylsulfonyl)phenyl]-1-benzofuran-2-sulfonamide;
N-[5-chloro-2-(phenylsulfinyl)phenyl]-1-benzofuran-2-sulfonamide;
2-[(1-benzofuran-2-ylsulfonyl)amino]-4-chloro-N-phenylbenzamide;
N-(5-chloro-2-cyanophenyl)-1-benzofuran-2-sulfonamide;
N-[5-chloro-2-(phenylacetyl)phenyl]-1-benzofuran-2-sulfonamide;
N-{5-chloro-2-[(1Z)-N-methoxy-2-phenylethanimidoyl]phenyl}-1-benzofuran-2-sulfonamide;
N-{5-chloro-2-[(1Z)-N-hydroxy-2-phenylethanimidoyl]phenyl}-1-benzofuran-2-sulfonamide;
N-[5-chloro-2-(phenylethynyl)phenyl]-1-benzofuran-2-sulfonamide;
N-[5-chloro-2-(2-phenylethyl)phenyl]-1-benzofuran-2-sulfonamide;
N-{5-chloro-2-[(Z)-2-phenylethenyl]phenyl}-1-benzofuran-2-sulfonamide;
N-[5-methyl-2-(phenylsulfanyl)phenyl]-1-benzofuran-2-sulfonamide;
N-[5-methyl-2-(phenylsulfinyl)phenyl]-1-benzofuran-2-sulfonamide;
N-[5-methyl-2-(phenylsulfonyl)phenyl]-1-benzofuran-2-sulfonamide;
N-[5-fluoro-2-(phenylsulfanyl)phenyl]-1-benzofuran-2-sulfonamide;
N-[5-fluoro-2-(phenylsulfinyl)phenyl]-1-benzofuran-2-sulfonamide;
N-[5-fluoro-2-(phenylsulfonyl)phenyl]-1-benzofuran-2-sulfonamide;
2-({2-[(1-benzofuran-2-ylsulfonyl)amino]-4-chlorophenyl}sulfanyl)benzoic acid;
3-({2-[(1-benzofuran-2-ylsulfonyl)amino]-4-chlorophenyl}sulfanyl)benzoic acid; and
4-({2-[(1-benzofuran-2-ylsulfonyl)amino]-4-chlorophenyl}sulfanyl)benzoic acid.

* * * * *

UNITED STATES PATENT AND TRADEMARK OFFICE
CERTIFICATE OF CORRECTION

PATENT NO. : 9,550,746 B2
APPLICATION NO. : 14/589681
DATED : January 24, 2017
INVENTOR(S) : Haiqing Yuan et al.

It is certified that error appears in the above-identified patent and that said Letters Patent is hereby corrected as shown below:

On the Title Page

On the page 2, in Column 2, item (56) under "Other Publications", Line 7, delete "Nofitication" and insert -- Notification --, therefor.

In the Specification

In Column 1, Line 43, delete "atheroscelorsis" and insert -- atherosclerosis --, therefor.

In Column 5, Line 54, after "$S(O)_2$" insert -- ; --.

In Column 9, Line 19, after "atom" insert -- . --.

In Column 10, Line 52, delete "Stahal" and insert -- Stahl --, therefor.

In Column 10, Line 53, delete "Chemica" and insert -- Chimica --, therefor.

In Column 10, Line 61, delete "Stahal" and insert -- Stahl --, therefor.

In Column 10, Line 62, delete "Chemica" and insert -- Chimica --, therefor.

In Column 11, Lines 32-33, delete "orchiectomyatopic" and insert -- orchiectomy atopic --, therefor.

In Column 11, Line 64, delete "vasuclar" and insert -- vascular --, therefor.

In Column 12, Line 16, delete "(PONS)," and insert -- (POHS), --, therefor.

In Column 12, Line 24, delete "accosiated" and insert -- associated --, therefor.

Signed and Sealed this
Fourteenth Day of March, 2017

Michelle K. Lee
*Director of the United States Patent and Trademark Office*

CERTIFICATE OF CORRECTION (continued)
U.S. Pat. No. 9,550,746 B2

In Column 12, Line 42, delete "pigement" and insert -- pigment --, therefor.

In Column 13, Line 3, delete "vasuclar" and insert -- vascular --, therefor.

In Column 13, Line 24, delete "(PONS)," and insert -- (POHS), --, therefor.

In Column 13, Line 31, delete "accosiated" and insert -- associated --, therefor.

In Column 13, Line 49, delete "pigement" and insert -- pigment --, therefor.

In Column 16, Line 62, delete "diasteroisomeric" and insert -- diastereoisomeric --, therefor.

In Column 17, Line 58, delete "add" and insert -- acid --, therefor.

In Column 32, Line 6, delete "CDCL$_3$)" and insert -- CDCl$_3$) --, therefor.

In Column 32, Line 40, delete "CDCL$_3$)" and insert -- CDCl$_3$) --, therefor.

In Column 32, Line 42, delete "7.85Hz," and insert -- 7.85 Hz, --, therefor.

In Column 36, Line 13, delete "[((Z)" and insert -- [(Z) --, therefor.

In Column 38, Line 40, delete "OH)," and insert -- 0H), --, therefor.

In Column 41, Line 4, delete "CDCl)" and insert -- CDCl$_3$) --, therefor.

In Column 49, Line 14, delete "4chlorophenoxy}" and insert -- 4-chlorophenoxy} --, therefor.

In Column 50, Line 39, delete "(2.69g," and insert -- (2.69 g, --, therefor.

In Column 53, Line 13, delete "4chlorophenoxy}" and insert -- 4-chlorophenoxy} --, therefor.

In Column 54, Line 15, delete "pg/ml" and insert -- µg/ml --, therefor.

In Column 54, Line 21, delete "MuItiPROBE" and insert -- MultiPROBE --, therefor.